(12) United States Patent
Lee et al.

(10) Patent No.: US 9,548,456 B2
(45) Date of Patent: Jan. 17, 2017

(54) ORGANIC COMPOUND AND ORGANIC LIGHT EMITTING DIODE DEVICE INCLUDING THE SAME

(71) Applicant: Samsung Display Co., Ltd., Yongin, Gyeonggi-do (KR)

(72) Inventors: Eun-Young Lee, Yongin (KR); Seok-Hwan Hwang, Yongin (KR); Young-Kook Kim, Yongin (KR); Hye-Jin Jung, Yongin (KR); Jun-Ha Park, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 0 days.

(21) Appl. No.: 13/958,316

(22) Filed: Aug. 2, 2013

(65) Prior Publication Data
US 2014/0306190 A1 Oct. 16, 2014

(30) Foreign Application Priority Data
Apr. 12, 2013 (KR) ........................ 10-2013-0040656

(51) Int. Cl.
| | | |
|---|---|---|
| C07B 59/00 | (2006.01) |
| C07C 13/66 | (2006.01) |
| C07C 22/08 | (2006.01) |
| C07C 25/22 | (2006.01) |
| C07C 255/51 | (2006.01) |
| C07D 209/86 | (2006.01) |
| C07D 213/53 | (2006.01) |
| C07D 215/04 | (2006.01) |
| C07D 251/24 | (2006.01) |
| C07D 307/91 | (2006.01) |
| C07D 333/76 | (2006.01) |
| C07D 401/14 | (2006.01) |
| C07F 5/02 | (2006.01) |
| C07F 7/08 | (2006.01) |
| C09K 11/06 | (2006.01) |
| H01L 51/00 | (2006.01) |
| H01L 51/50 | (2006.01) |

(52) U.S. Cl.
CPC ......... *H01L 51/0054* (2013.01); *C07B 59/001* (2013.01); *C07C 13/66* (2013.01); *C07C 22/08* (2013.01); *C07C 25/22* (2013.01); *C07C 255/51* (2013.01); *C07D 209/86* (2013.01); *C07D 213/53* (2013.01); *C07D 215/04* (2013.01); *C07D 251/24* (2013.01); *C07D 307/91* (2013.01); *C07D 333/76* (2013.01); *C07D 401/14* (2013.01); *C07F 5/025* (2013.01); *C07F 7/0809* (2013.01); *C09K 11/06* (2013.01); *H01L 51/0058* (2013.01); *C07C 2103/18* (2013.01); *C07C 2103/24* (2013.01); *C07C 2103/26* (2013.01); *C07C 2103/40* (2013.01); *C07C 2103/50* (2013.01); *C07C 2103/94* (2013.01); *C09K 2211/1011* (2013.01); *H01L 51/0067* (2013.01); *H01L 51/5012* (2013.01); *H01L 51/5072* (2013.01)

(58) Field of Classification Search
CPC ............ H01L 51/0054; H01L 51/0067; H01L 51/5012; H01L 51/0058; H01L 51/5072; C07C 13/547; C07C 13/32; C07C 13/00; C07C 13/66; C07C 22/08; C07C 25/22; C07C 255/51; C07C 2103/18; C07C 2103/24; C07C 2103/26; C07C 2103/40; C07C 2103/50; C07C 2103/94; C07B 59/001; C07D 209/86; C07D 213/53; C07D 215/04; C07D 251/24; C07D 307/91; C07D 333/76; C07D 401/14; C07F 5/025; C07F 7/0809; C09K 11/06; C09K 2211/1011
USPC ............... 544/180; 585/27; 546/255; 257/40
See application file for complete search history.

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,596,415 | B2 | 7/2003 | Shi et al. |
| 7,781,579 | B2 * | 8/2010 | Park ....................... C07C 211/54 544/101 |
| 8,398,895 | B2 | 3/2013 | Sparrowe et al. |

(Continued)

FOREIGN PATENT DOCUMENTS

| | | |
|---|---|---|
| JP | 1996-12600 A | 1/1996 |
| JP | 2000-3782 A | 1/2000 |

(Continued)

OTHER PUBLICATIONS

Park et al., "A Blue-Light Emitting Polymer with a Rigid Backbone for Enhanced Color Stability," Advanced Functional Materials, 17(16), 2007, 3063-3068.*

(Continued)

*Primary Examiner* — Paul A Zucker
*Assistant Examiner* — Mark Luderer
(74) *Attorney, Agent, or Firm* — Knobbe Martens Olson & Bear LLP

(57) ABSTRACT

Disclosed are a novel organic compound and an organic light emitting diode device using the same. More particularly, a novel organic compound having electrical stability, high charge transport capability, and light emitting performance, high glass transition temperature and being capable of preventing crystallization, and an organic light emitting diode device including an organic layer including the same are disclosed.

9 Claims, 1 Drawing Sheet

(56) References Cited

U.S. PATENT DOCUMENTS

| | | | |
|---|---|---|---|
| 2005/0074631 A1* | 4/2005 | Ishida et al. | 428/690 |
| 2008/0093987 A1* | 4/2008 | Park et al. | 313/504 |
| 2012/0007059 A1 | 1/2012 | Iwakuma et al. | |
| 2012/0104369 A1 | 5/2012 | Kawata et al. | |
| 2013/0270524 A1* | 10/2013 | Park et al. | 257/40 |
| 2013/0328021 A1* | 12/2013 | Lim et al. | 257/40 |
| 2014/0014925 A1* | 1/2014 | Jung et al. | 257/40 |
| 2014/0209872 A1* | 7/2014 | Park et al. | 257/40 |

FOREIGN PATENT DOCUMENTS

| | | |
|---|---|---|
| KR | 10-2011-0114547 A | 10/2011 |
| KR | 10-2012-0036898 A | 4/2012 |

OTHER PUBLICATIONS

Song et al., "Novel cyclopenta[def]phenanthrene based blue emitting oligomers for OLEDs," Tetrahedron Letters 49 (2008), 3582-3587.*

\* cited by examiner

ORGANIC COMPOUND AND ORGANIC LIGHT EMITTING DIODE DEVICE INCLUDING THE SAME

CROSS-REFERENCE TO RELATED APPLICATIONS

This application claims priority to and the benefit of Korean Patent Application No. 10-2013-0040656 filed in the Korean Intellectual Property Office on Apr. 12, 2013, the entire contents of which are incorporated herein by reference.

BACKGROUND

Field

An organic compound and an organic light emitting diode device are disclosed.

Description of the Related Technology

Recently, demand for reduced size and thickness of a monitor, a television, or the like has promoted replacement of a cathode ray tube (CRT) with a liquid crystal display (LCD). However, the liquid crystal display (LCD) does not only need a separate backlight as a non-emissive device but is also limited in terms of a response speed, viewing angle, and the like. Recently, organic light emitting diode devices have been contemplated as a display device to overcome such limits. The organic light emitting diode device is a self-light emitting display device having a wide viewing angle, improved contrasts and a fast response time. An organic light emitting diode device includes two electrodes and an emission layer disposed therebetween and emits light when electrons injected from one electrode are combined with holes injected from the other electrode and thus, form excitons and emit energy.

SUMMARY

One embodiment provides a novel organic compound that is applicable to an organic light emitting diode device.

Another embodiment provides an organic light emitting diode device including the organic compound.

One embodiment provides an organic compound represented by the following Chemical Formula 1.

Chemical Formula 1

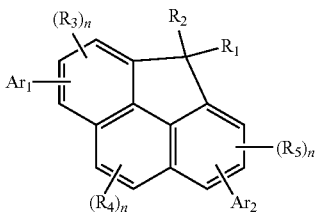

In the above Chemical Formula 1, $R_1$ and $R_2$ may independently be hydrogen, deuterium, a substituted or unsubstituted $C_1$ to $C_{30}$ alkyl group, a substituted or unsubstituted $C_2$ to $C_{30}$ alkenyl group, a substituted or unsubstituted $C_2$ to $C_{30}$ alkynyl group, a substituted or unsubstituted $C_3$ to $C_{30}$ cycloalkyl group, a substituted or unsubstituted $C_1$ to $C_{30}$ alkoxy group, a substituted or unsubstituted $C_6$ to $C_{30}$ aryloxy group, a substituted or unsubstituted $C_6$ to $C_{30}$ arylthiol group, a substituted or unsubstituted $C_6$ to $C_{30}$ aryl group, an amino group substituted with a $C_6$ to $C_{30}$ aryl group or a $C_2$ to $C_{30}$ heteroaryl group, a substituted or unsubstituted $C_2$ to $C_{30}$ heteroaryl group, a halogen, a cyano group, a nitro group, a hydroxy group, a carboxyl group, or a combination thereof, or $R_1$ and $R_2$ are linked to each other to form a ring, $R_3$ to $R_5$ may independently be hydrogen, deuterium, a substituted or unsubstituted $C_1$ to $C_{30}$ alkyl group, a substituted or unsubstituted $C_2$ to $C_{30}$ alkenyl group, a substituted or unsubstituted $C_2$ to $C_{30}$ alkynyl group, a substituted or unsubstituted $C_3$ to $C_{30}$ cycloalkyl group, a substituted or unsubstituted $C_1$ to $C_{30}$ alkoxy group, a substituted or unsubstituted $C_6$ to $C_{30}$ aryloxy group, a substituted or unsubstituted $C_6$ to $C_{30}$ arylthiol group, a substituted or unsubstituted $C_6$ to $C_{30}$ aryl group, an amino group substituted with a $C_6$ to $C_{30}$ aryl group or a $C_2$ to $C_{30}$ heteroaryl group, a substituted or unsubstituted $C_2$ to $C_{30}$ heteroaryl group, a halogen, a cyano group, a nitro group, a hydroxy group, a carboxyl group, or a combination thereof, n may be an integer ranging from 0 to 2, and $Ar_1$ and $Ar_2$ may independently be a substituted or unsubstituted $C_6$ to $C_{30}$ aryloxy group, a substituted or unsubstituted $C_6$ to $C_{30}$ arylthiol group, a substituted or unsubstituted $C_6$ to $C_{30}$ aryl group, an amino group substituted with a $C_6$ to $C_{30}$ aryl group or a $C_2$ to $C_{30}$ heteroaryl group, a substituted or unsubstituted $C_2$ to $C_{30}$ heteroaryl group, or a combination thereof.

Specifically, the $R_1$ and $R_2$ may independently be a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, or a combination thereof, or $R_1$ and $R_2$ are linked to each other to form a ring, and $Ar_1$ and $Ar_2$ may independently be a substituted or unsubstituted $C_6$ to $C_{30}$ aryl group, a substituted or unsubstituted $C_2$ to $C_{30}$ heteroaryl group, or a combination thereof.

More specifically, the $R_1$ and $R_2$ may independently be a substituted or unsubstituted $C_1$ to $C_{30}$ alkyl group, or a substituted or unsubstituted $C_1$ to $C_{30}$ aryl group, or $R_1$ and $R_2$ are linked to each other to form a ring, and $Ar_1$ and $Ar_2$ may independently be a substituted or unsubstituted phenyl group, a substituted or unsubstituted biphenyl group, a substituted or unsubstituted terphenyl group, a substituted or unsubstituted naphthalene group, a substituted or unsubstituted anthracene group, a substituted or unsubstituted phenanthrene group, a substituted or unsubstituted pyrene group, a substituted or unsubstituted fluorene group, a substituted or unsubstituted carbazole group, a substituted or unsubstituted dibenzofuran, a substituted or unsubstituted dibenzothiophene, a substituted or unsubstituted pyridine group, or a combination thereof.

The compound represented by the above Chemical Formula 1 may be an organic compound including at least one selected from the compound listed in the following Group 1.

Another embodiment provides an organic light emitting diode device that includes an anode, a cathode, and an organic layer interposed between the anode and cathode, wherein the organic layer includes the organic compound represented by the above Chemical Formula 1.

The organic layer may include an emission layer, and the organic compound represented by the above Chemical Formula 1 may be included in the emission layer.

The emission layer may further include anthracene, arylamine, styrene, a derivative thereof, or a combination thereof.

The emission layer may include the organic compound represented by the above Chemical Formula 1 as a fluorescent or phosphorescent host.

The organic layer may include an emission layer and an auxiliary layer interposed between the emission layer and the cathode, and the organic compound represented by the above Chemical Formula 1 may be included in the auxiliary layer.

The emission layer may include anthracene, arylamine, styrene, a derivative thereof, or a combination thereof.

Other embodiments are included in the following detailed description.

BRIEF DESCRIPTION OF THE DRAWING

FIG. 1 shows the structure of an organic light emitting diode device according to one embodiment.

DETAILED DESCRIPTION

Hereinafter, the present disclosure will be described more fully hereinafter with reference to the accompanying drawings, in which example embodiments of this disclosure are shown. However, this disclosure may, however, be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it may be directly on the other element or intervening elements may also be present. In contrast, when an element is referred to as being "directly on" another element, there are no intervening elements present.

As used herein, when a definition is not otherwise provided, the term "substituted" refers to one substituted with a substituent selected from deuterium, a $C_1$ to $C_{30}$ alkyl group, a $C_6$ to $C_{36}$ aryl group, a $C_2$ to $C_{30}$ heteroaryl group, a $C_1$ to $C_{30}$ alkoxy group, a $C_2$ to $C_{30}$ alkenyl group, a $C_6$ to $C_{30}$ aryloxy group, a $C_3$ to $C_{40}$ silyloxy group, a $C_1$ to $C_{30}$ acyl group, a $C_2$ to $C_{30}$ acyloxy group, a $C_2$ to $C_{30}$ heteroaryloxy group, a $C_1$ to $C_{30}$ sulfonyl group, a $C_1$ to $C_{30}$ alkylthio group, a $C_6$ to $C_{30}$ arylthio group, a $C_1$ to $C_{30}$ heterocyclothiol group, a $C_1$ to $C_{30}$ phosphoric acid amide group, a $C_3$ to $C_{40}$ silyl group, NRR' (wherein, R and R' are each independently a substituent selected from hydrogen, a $C_1$ to $C_{30}$ alkyl group and a $C_6$ to $C_{30}$ aryl group), a carboxyl group, a halogen, a cyano group, a nitro group, an azo group, a fluorene group, and a hydroxy group, instead of at least one hydrogen.

The $C_6$ to $C_{36}$ aryl group, $C_2$ to $C_{30}$ heteroaryl group, and fluorene group may be further substituted with a substituent selected from deuterium, a halogen, a cyano group, a methyl group, a trifluoromethyl group, and a phenyl group.

As used herein, when a definition is not otherwise provided, the term "hetero" refers to 1 to 3 heteroatoms selected from N, O, S, and P, and remaining carbon in one ring.

As used herein, the "organic layer" may refer to a layer including an organic material, but the organic layer is not a layer consisting of an organic material, may include an inorganic material, a metal complex, and the like as well as an organic material, and may include at least one layer.

Representative groups in the chemical formulae of the present embodiments are defined as follows (carbon numbers of substituents are not limited and do not limit characteristics of substituents).

The unsubstituted $C_1$ to $C_{30}$ alkyl group may be linear and branched, and non-limiting examples thereof may be methyl, ethyl, propyl, isobutyl, sec-butyl, pentyl, iso-amyl, hexyl, heptyl, octyl, nonyl, dodecyl, and the like.

The unsubstituted $C_2$ to $C_{30}$ alkenyl group may have at least one carbon double bond in the middle or terminal end of the unsubstituted alkyl group. Examples thereof may be ethenyl, propenyl, butenyl, and the like.

The unsubstituted $C_2$ to $C_{30}$ alkynyl group may have at least one carbon triple bond in the middle or terminal end of the unsubstituted alkyl group. Examples thereof may be acetylene, propylene, phenylacetylene, naphthylacetylene, isopropylacetylene, t-butylacetylene, diphenylacetylene, and the like.

The unsubstituted $C_3$ to $C_{30}$ cycloalkyl group may refer to a cyclic alkyl group having 3 to 30 carbon numbers.

The unsubstituted $C_1$ to $C_{30}$ alkoxy group may refer to —OA (wherein, A is the above-described unsubstituted $C_1$ to $C_{30}$, and non-limiting examples may be methoxy, ethoxy, propoxy, isopropyloxy, butoxy, pentoxy, and the like.

The unsubstituted $C_6$ to $C_{30}$ aryl group may refer to a carbocycle aromatic system having at least one ring. The aryl group may have two or more rings, which may be fused or linked through a single bond and the like. The term aryl may include an aromatic system such as phenyl, naphthyl, anthracenyl, and the like. The unsubstituted $C_6$ to $C_{30}$ $C_6$ to $C_{30}$ aryl group may be selected from a phenyl group, a tolyl group, a naphthyl group, an anthracenyl group, a terphenyl group, a phenanthrenyl group, a pyrenyl group, a diphenylanthracenyl group, a dinaphthylanthracenyl group, a pentacenyl group, a bromophenyl group, a hydroxyphenyl group, a stilbene group, an azobenzenyl group, and a ferrocenyl group.

The unsubstituted $C_2$ to $C_{30}$ heteroaryl group may include 1, 2 or 3 heteroatoms selected from N, O, S, and P. The heteroaryl group may have two or more rings, which may be fused or linked through a single bond and the like. Examples of the unsubstituted $C_2$ to $C_{30}$ heteroaryl group may be selected from a pyrazolyl group, an imidazolyl group, an oxazolyl group, a thiazolyl group, a triazinyl group, a triazolyl group, a tetrazolyl group, an oxadiazolyl group, a thiadiazolyl group, a pyridinyl group, a pyridazinyl group, pyrimidinyl group, a triazinyl group, a carbazolyl group, an indolyl group, a quinolinyl group, an isoquinolinyl group, a thiophene group, a dibenzothiophene group, a dibenzofuran group, and a benzimidazolyl group.

The unsubstituted $C_6$ to $C_{30}$ aryloxy group may refer to —$OA_1$, wherein $A_1$ is the same functional group as the $C_6$ to $C_{30}$ $C_6$ to $C_{30}$ aryl group except carbon numbers. Examples of the aryloxy group may include a phenoxy group, and the like.

The unsubstituted $C_6$ to $C_{30}$ arylthio group may refer to —$SA_1$, wherein $A_1$ is the same functional group as the $C_6$ to $C_{30}$ aryl group except carbon numbers. Examples of the arylthio group may include a benzenethio group, a naphthylthio group, and the like.

Hereinafter, one embodiment and another embodiment are described in detail.

An organic compound according to one embodiment is represented by the following Chemical Formula 1:

Chemical Formula 1

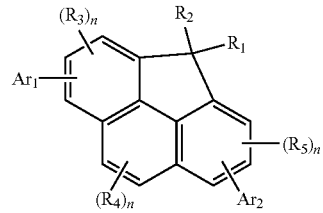

In the above Chemical Formula 1, $R_1$ and $R_2$ may independently be hydrogen, deuterium, a substituted or unsubstituted $C_1$ to $C_{30}$ alkyl group, a substituted or unsubstituted $C_2$ to $C_{30}$ alkenyl group, a substituted or unsubstituted $C_2$ to $C_{30}$ alkynyl group, a substituted or unsubstituted $C_3$ to $C_{30}$ cycloalkyl group, a substituted or unsubstituted $C_1$ to $C_{30}$ alkoxy group, a substituted or unsubstituted $C_6$ to $C_{30}$ aryloxy group, a substituted or unsubstituted $C_6$ to $C_{30}$ arylthiol group, a substituted or unsubstituted $C_6$ to $C_{30}$ aryl group, an amino group substituted with a $C_6$ to $C_{30}$ aryl group or a $C_2$ to $C_{30}$ heteroaryl group, a substituted or unsubstituted $C_2$ to $C_{30}$ heteroaryl group, a halogen, a cyano group, a nitro group, a hydroxy group, a carboxyl group, or a combination thereof, or $R_1$ and $R_2$ are linked to each other to form a ring, $R_3$ to $R_5$ may independently be hydrogen, deuterium, a substituted or unsubstituted $C_1$ to $C_{30}$ alkyl group, a substituted or unsubstituted $C_2$ to $C_{30}$ alkenyl group, a substituted or unsubstituted $C_2$ to $C_{30}$ alkynyl group, a substituted or unsubstituted $C_3$ to $C_{30}$ cycloalkyl group, a substituted or unsubstituted $C_1$ to $C_{30}$ alkoxy group, a substituted or unsubstituted $C_6$ to $C_{30}$ aryloxy group, a substituted or unsubstituted $C_6$ to $C_{30}$ arylthiol group, a substituted or unsubstituted $C_6$ to $C_{30}$ aryl group, an amino group substituted with a $C_6$ to $C_{30}$ aryl group or a $C_2$ to $C_{30}$ heteroaryl group, a substituted or unsubstituted $C_2$ to $C_{30}$ heteroaryl group, a halogen, a cyano group, a nitro group, a hydroxy group, a carboxyl group, or a combination thereof, n may be an integer ranging from 0 to 2, and $Ar_1$ and $Ar_2$ may independently be a substituted or unsubstituted $C_6$ to $C_{30}$ aryloxy group, a substituted or unsubstituted $C_6$ to $C_{30}$ arylthiol group, a substituted or unsubstituted $C_6$ to $C_{30}$ aryl group, an amino group substituted with a $C_6$ to $C_{30}$ aryl group or a $C_2$ to $C_{30}$ heteroaryl group, a substituted or unsubstituted $C_2$ to $C_{30}$ heteroaryl group, or a combination thereof.

Specifically, the $R_1$ and $R_2$ may independently be a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heteroaryl group, or a combination thereof, or $R_1$ and $R_2$ are linked to each other to form a ring, $Ar_1$ and $Ar_2$ are each independently a substituted or unsubstituted $C_6$ to $C_{30}$ aryl group, a substituted or unsubstituted $C_2$ to $C_{30}$ heteroaryl group, or a combination thereof.

More specifically, the $R_1$ and $R_2$ may independently be a substituted or unsubstituted $C_1$ to $C_{30}$ alkyl group, or a substituted or unsubstituted $C_1$ to $C_{30}$ aryl group, or $R_1$ and $R_2$ are linked to each other to form a ring, $Ar_1$ and $Ar_2$ may independently be a substituted or unsubstituted phenyl group, a substituted or unsubstituted biphenyl group, a substituted or unsubstituted terphenyl group, a substituted or unsubstituted naphthalene group, a substituted or unsubstituted anthracene group, a substituted or unsubstituted phenanthrene group, a substituted or unsubstituted pyrene group, a substituted or unsubstituted fluorene group, a substituted or unsubstituted carbazole group, a substituted or unsubstituted dibenzofuran, a substituted or unsubstituted dibenzothiophene, a substituted or unsubstituted pyridine group, or a combination thereof.

According to one embodiment, the organic compound represented by the above Chemical Formula 1 may function as a light emitting material or an electron transport material for an organic light emitting diode device.

The compound represented by the above Chemical Formula 1 may be, for example, a blue light emitting material, but is not limited thereto. The compound represented by the above Chemical Formula 1 includes at least one fused ring inside a molecule and thus, may increase a glass transition temperature (Tg) and a melting point and thereby, decrease Joule heat generated in an organic layer, between organic layers, and between the organic layer and a metal electrode and/or deterioration due to thermal stress at a high temperature when applied to an organic light emitting diode device.

Accordingly, the organic compound represented by the above Chemical Formula 1 may increase durability of the organic light emitting diode device during storage and operation. In addition, the organic compound represented by the above Chemical Formula 1 has an improved molecular film due to introduction of a substituent such as a fluorene group and the like and may improve characteristics of the organic light emitting diode device.

Examples of the compound represented by the above Chemical Formula 1 may be at least one compound listed in the following Group 1 (compounds represented by Chemical Formulae 2 to 70), but are not limited thereto. The compounds listed in the following Group 1 (compounds represented by Chemical Formulae 2 to 70) may be used singularly or in a mixture of at least two, and may be used in a mixture of another compound.

Group 1

Chemical Formula 2

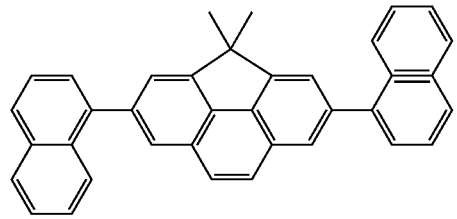

Chemical Formula 3

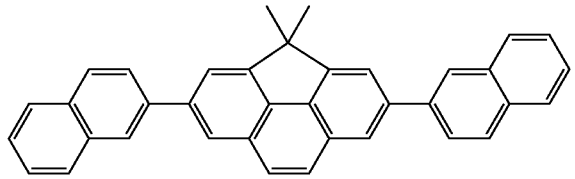

Chemical Formula 4

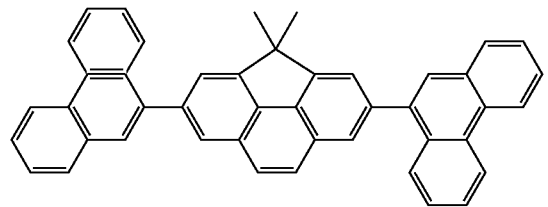

Chemical Formula 5

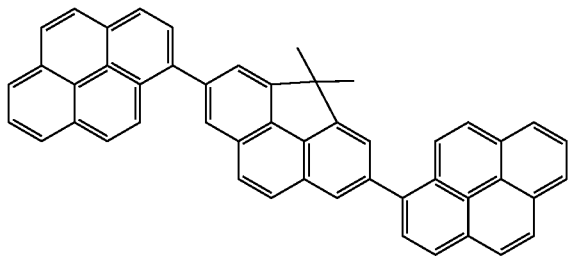

Chemical Formula 6

Chemical Formula 7

Chemical Formula 8

Chemical Formula 9

Chemical Formula 10

Chemical Formula 11

Chemical Formula 12

-continued
Chemical Formula 13
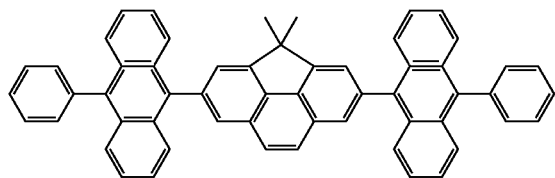
Chemical Formula 14
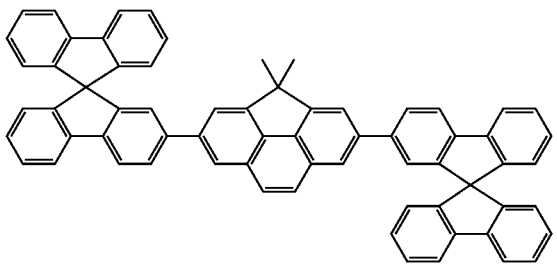
Chemical Formula 15
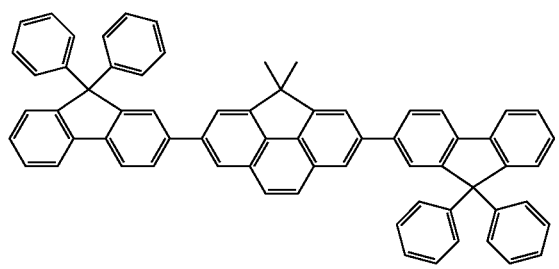
Chemical Formula 16
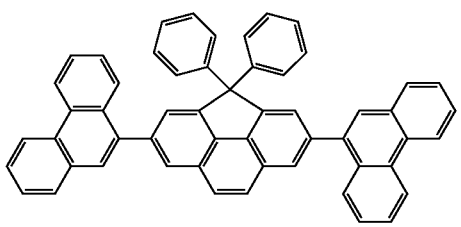
Chemical Formula 17
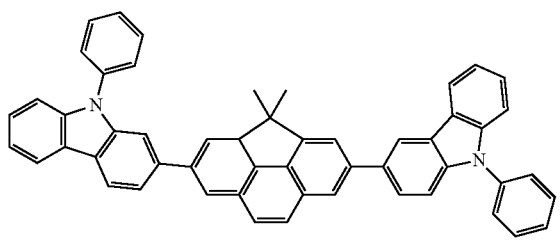
Chemical Formula 18
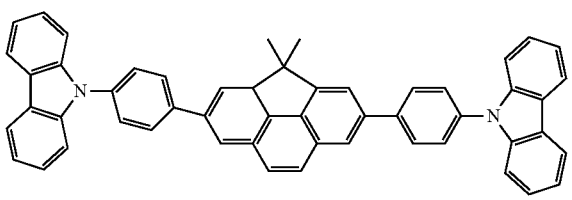
Chemical Formula 19
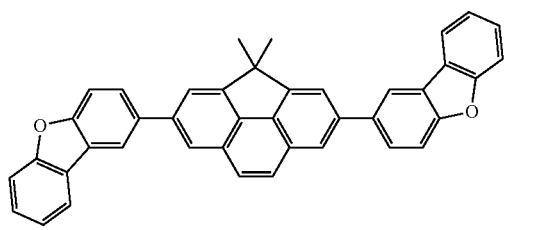
Chemical Formula 20
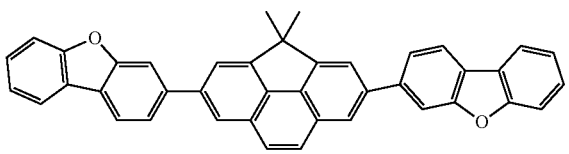
Chemical Formula 21
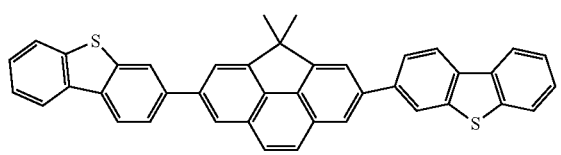
Chemical Formula 22
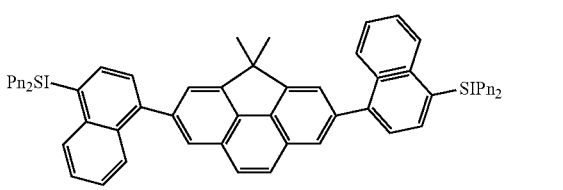
Chemical Formula 23
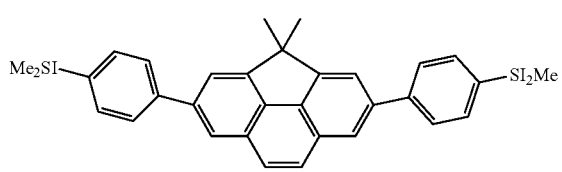
Chemical Formula 24
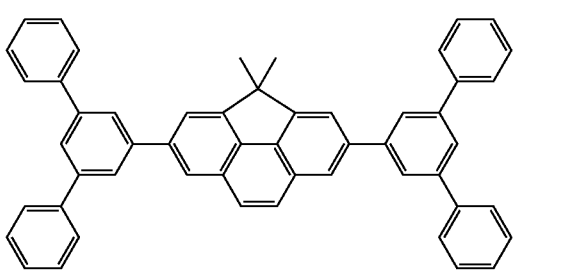

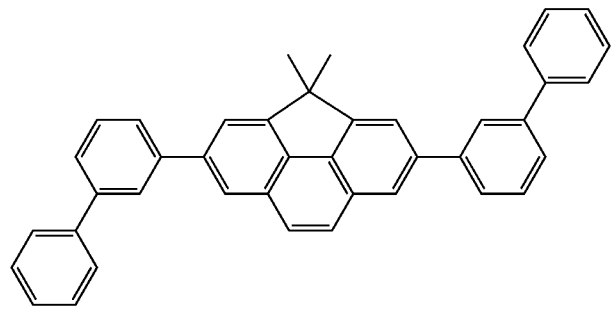
Chemical Formula 25
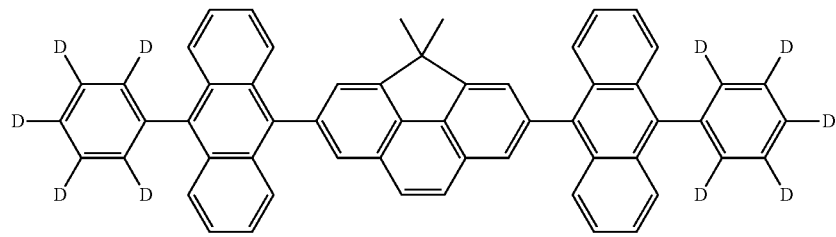
Chemical Formula 26
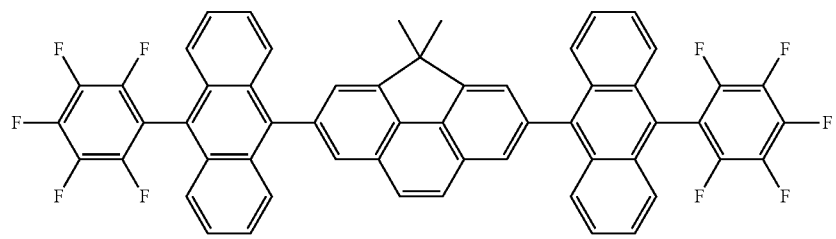
Chemical Formula 27
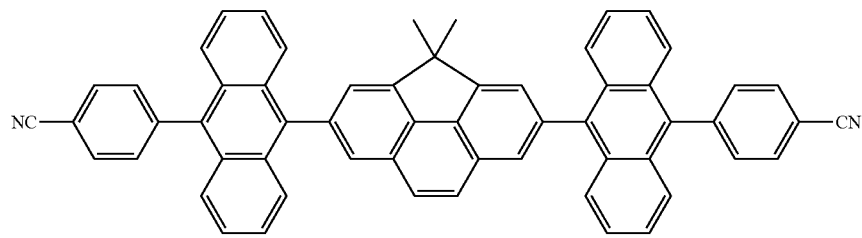
Chemical Formula 28
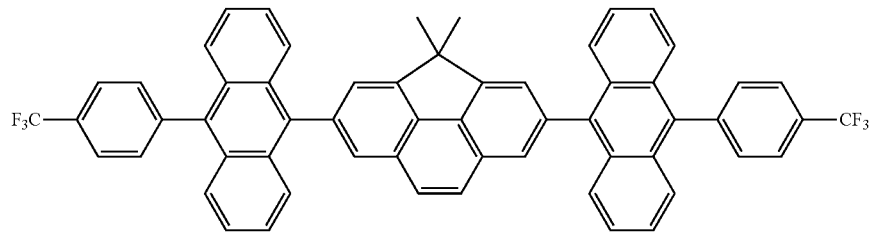
Chemical Formula 29
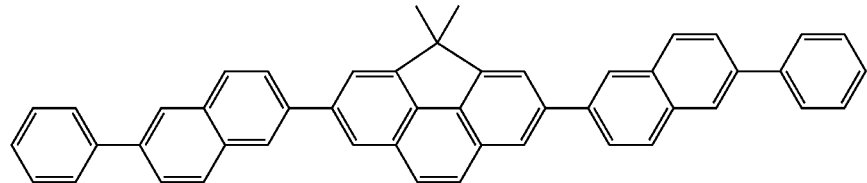
Chemical Formula 30

Chemical Formula 31
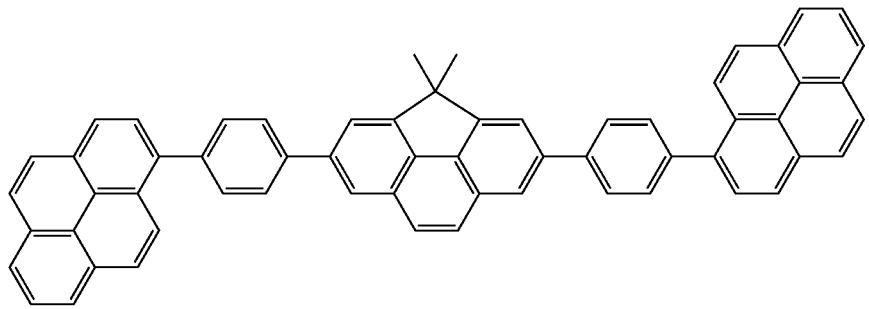
Chemical Formula 32
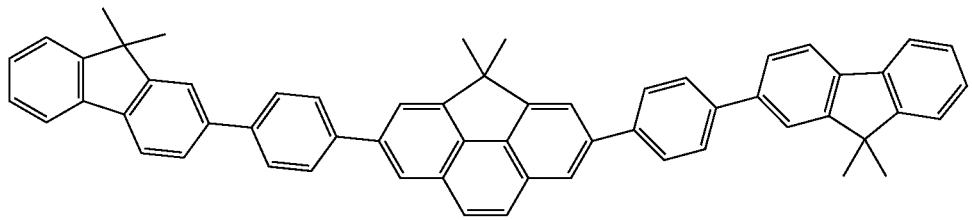
Chemical Formula 33
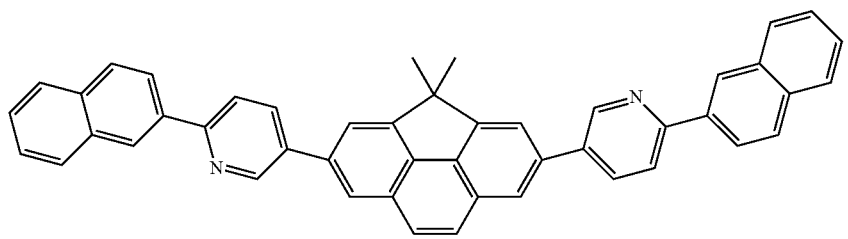
Chemical Formula 34
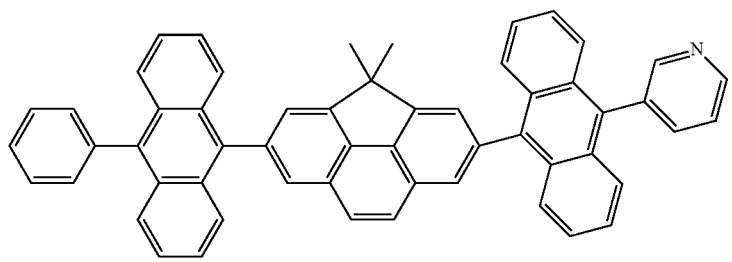
Chemical Formula 35
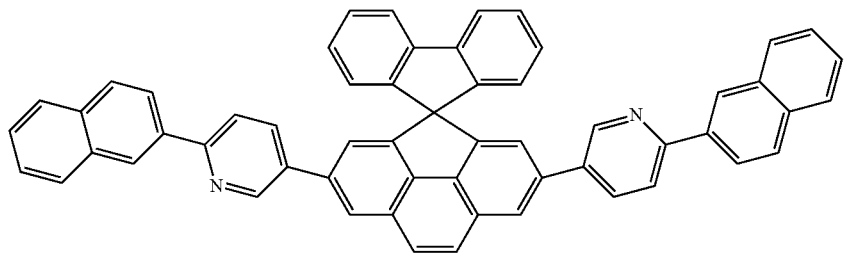
Chemical Formula 36
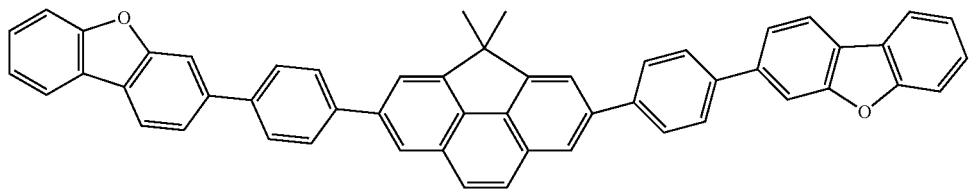

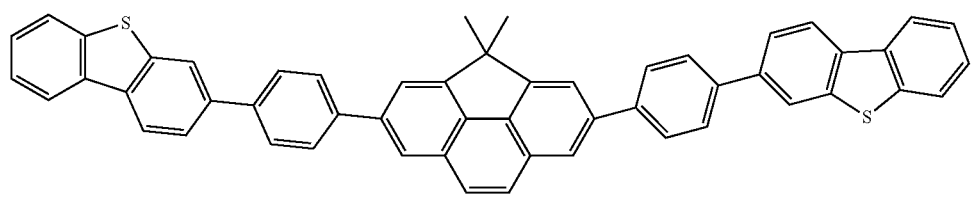
Chemical Formula 37
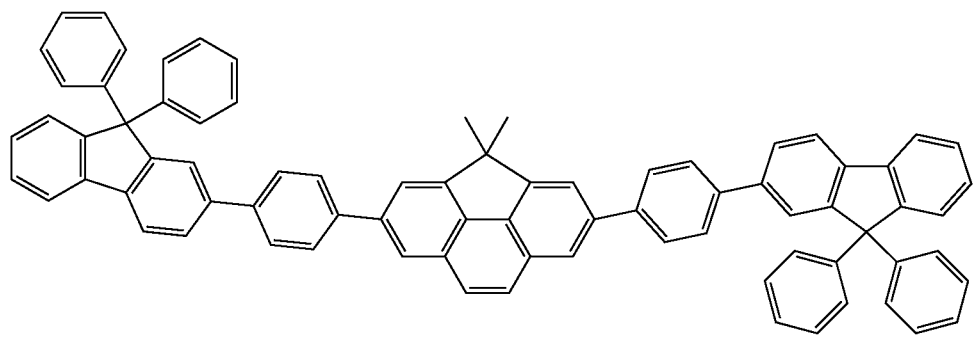
Chemical Formula 38
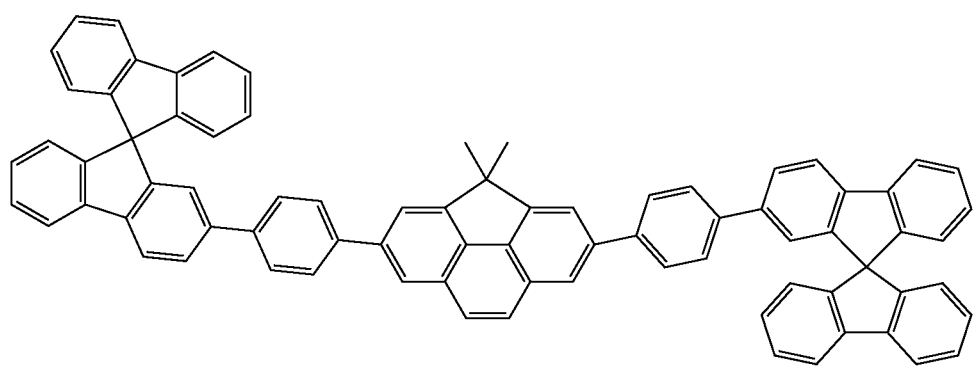
Chemical Formula 39
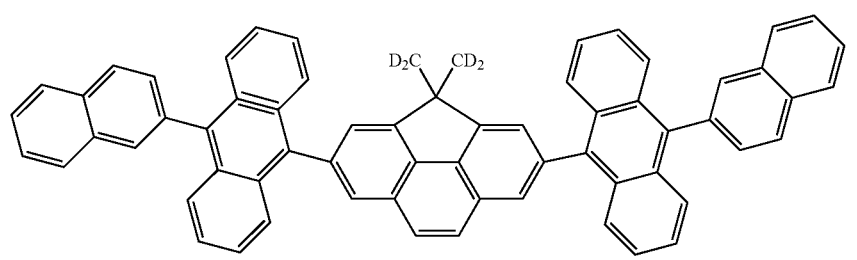
Chemical Formula 40
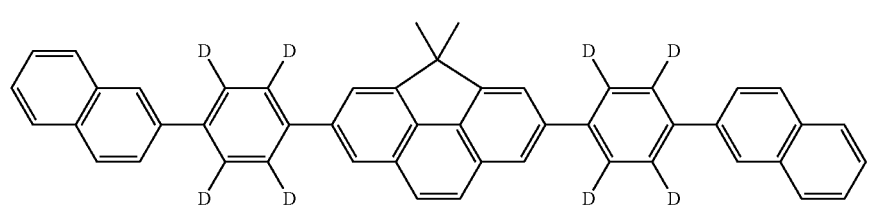
Chemical Formula 41
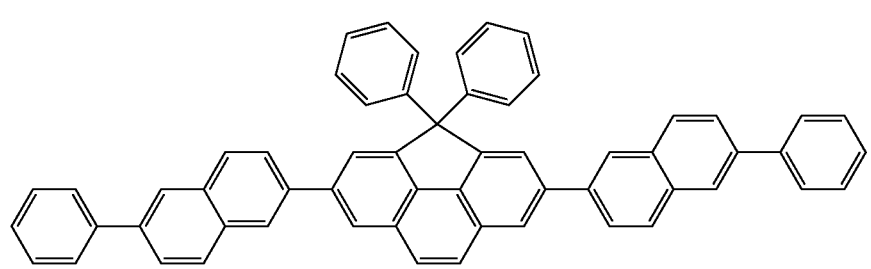
Chemical Formula 42

-continued
Chemical Formula 43
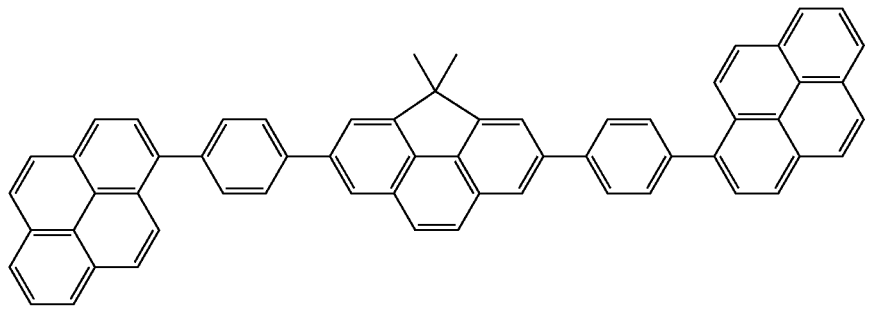
Chemical Formula 44
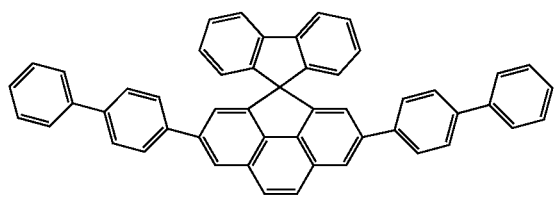
Chemical Formula 45
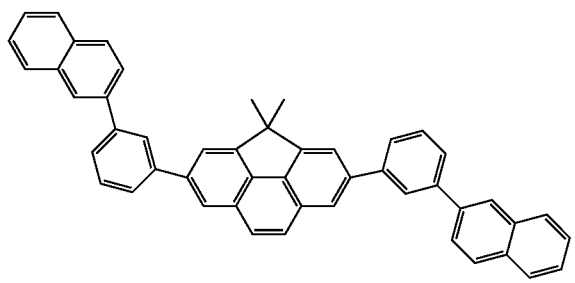
Chemical Formula 46
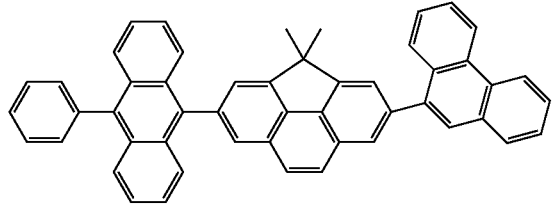
Chemical Formula 47
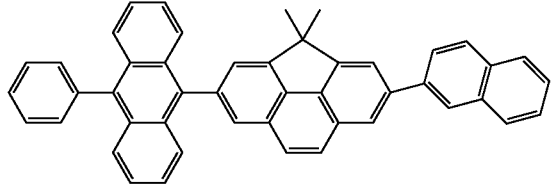
Chemical Formula 48
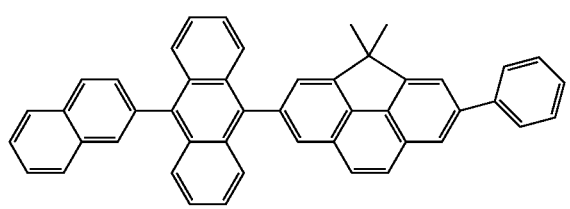
Chemical Formula 49
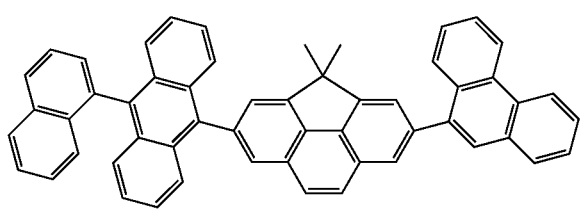
Chemical Formula 50
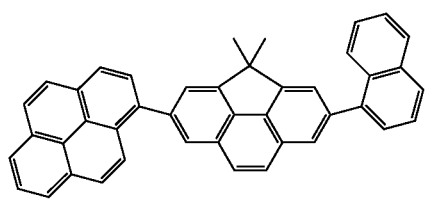
Chemical Formula 51
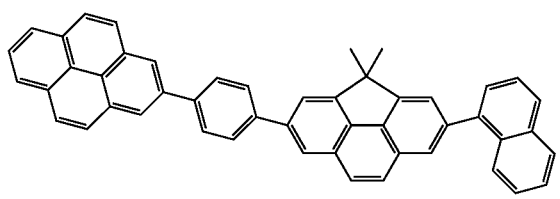
Chemical Formula 52
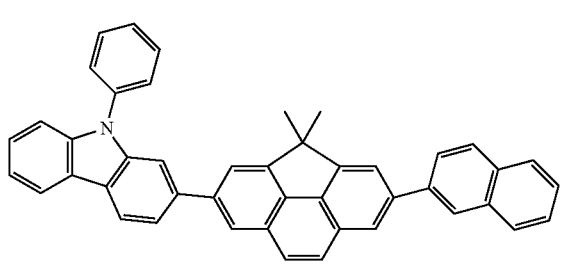
Chemical Formula 53
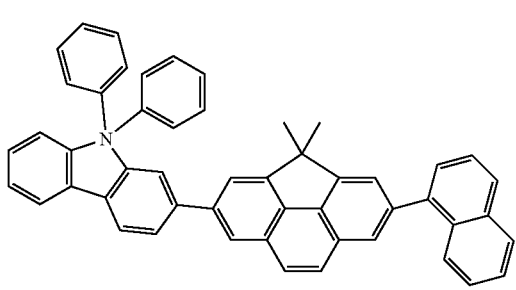

-continued
Chemical Formula 54
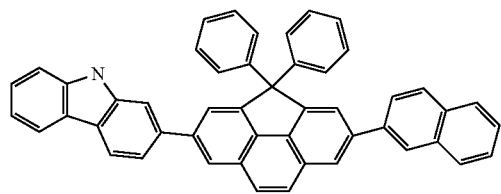
Chemical Formula 55
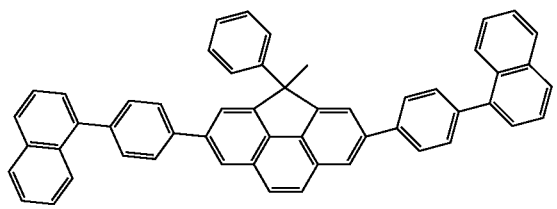
Chemical Formula 56
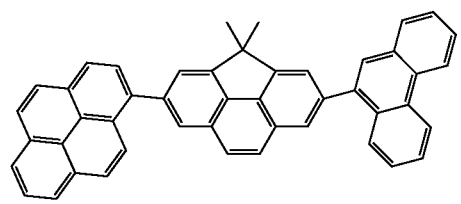
Chemical Formula 57
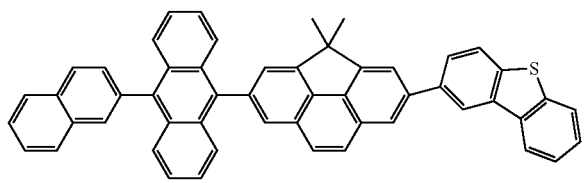
Chemical Formula 58
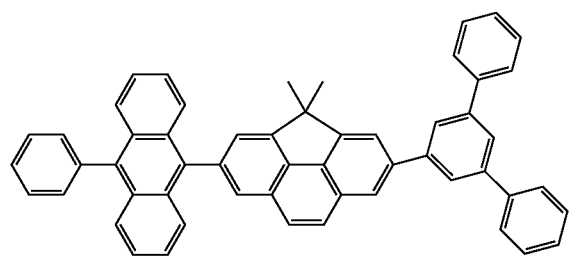
Chemical Formula 59
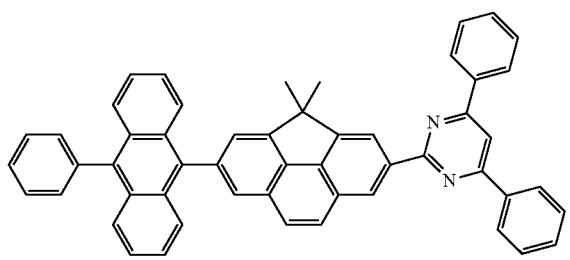
Chemical Formula 60
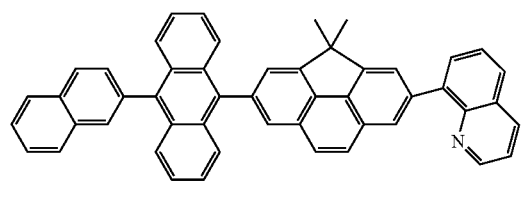
Chemical Formula 61
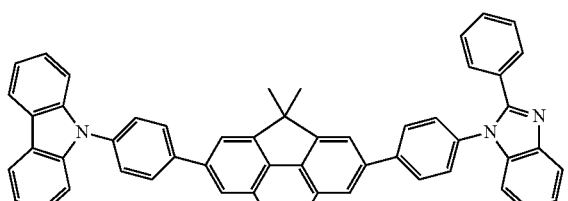
Chemical Formula 62
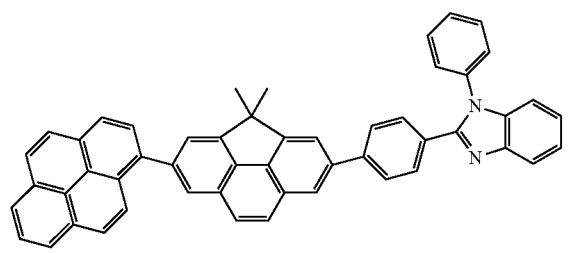
Chemical Formula 63
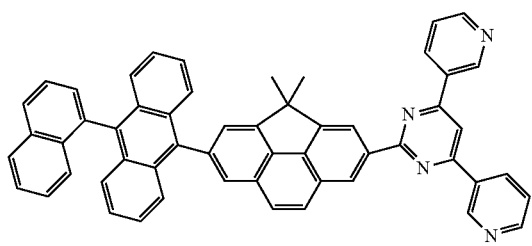

-continued
Chemical Formula 64
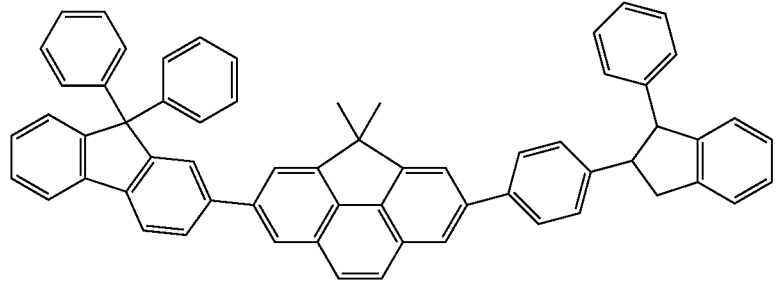
Chemical Formula 65
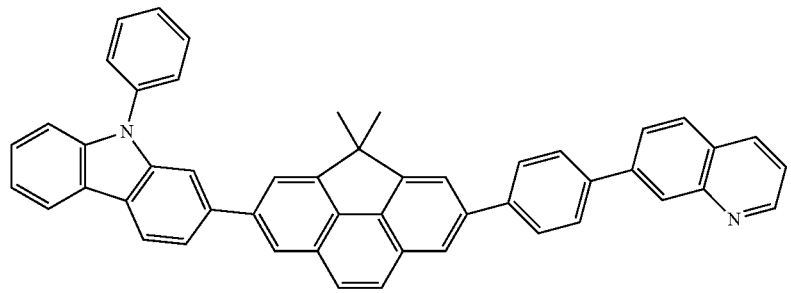
Chemical Formula 66
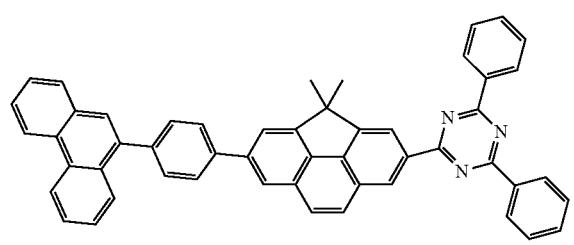
Chemical Formula 67
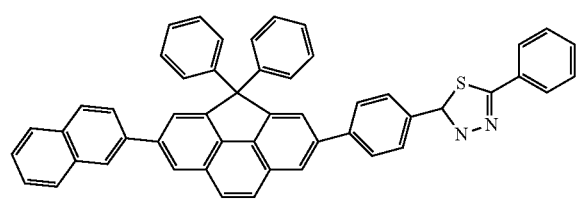
Chemical Formula 68
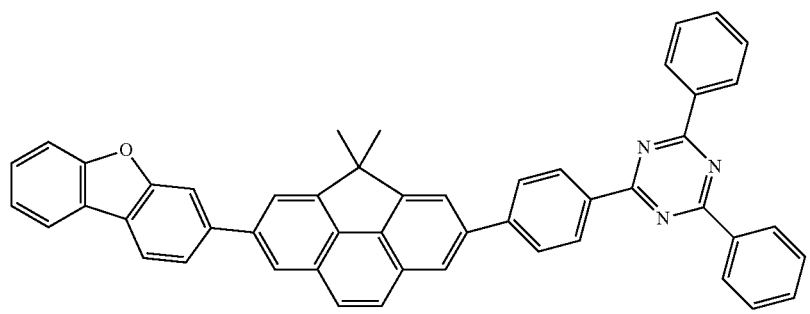
Chemical Formula 69
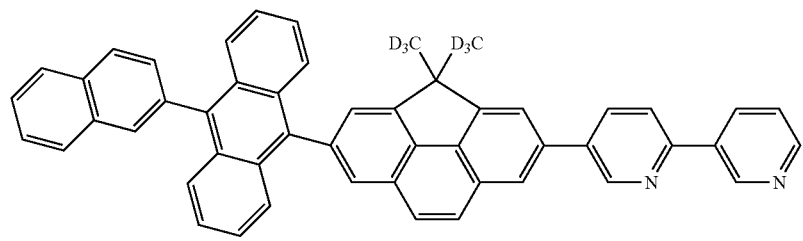

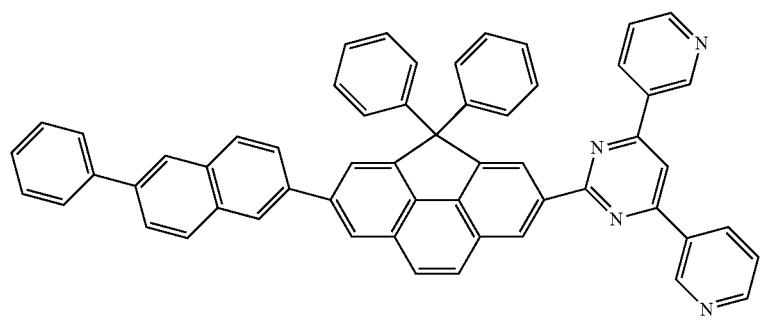

Chemical Formula 70

Hereinafter, an organic light emitting diode device including the organic compound according to one embodiment is described referring to FIG. 1.

FIG. 1 is a cross-sectional view of an organic light emitting diode device according to one embodiment.

Referring to FIG. 1, the organic light emitting diode device according to one embodiment includes an anode 1, a cathode 2 facing the anode 1, and an organic layer 10 interposed between the anode 1 and cathode 2.

The substrate (not shown) may be disposed on the side of anode 1 or on the side of cathode 2. The substrate may be made of an inorganic material such as glass or an organic material such as polycarbonate, polymethylmethacrylate, polyethyleneterephthalate, polyethylenenaphthalate, polyamide, polyethersulfone, or a combination thereof, silicon wafer, and the like.

One of the anode 1 and cathode 2 may be a transparent electrode, and the transparent electrode may comprise, for example conductive oxide such as indium tin oxide (ITO), indium zinc oxide (IZO), tin oxide ($SnO_2$), zinc oxide (ZnO), or a combination thereof, or a metal such as Al, Ag, or Mg in a thin thickness.

The organic layer 10 includes an emission layer 5, a hole auxiliary layer 3 interposed between the anode 1 and emission layer 5, and an electron auxiliary layer 4 interposed between the cathode 2 and emission layer 5. However, at least one of the hole auxiliary layer 3 and electron auxiliary layer 4 may be omitted.

The emission layer 5 may include the above-described organic compound. The organic compound may be used singularly or in a mixture and may be used in a mixture of another organic material. When the organic compound is mixed with another organic material, it may be function as a fluorescent or phosphorescent host, and may include well-known dopants.

A red dopant may include PtOEP, Ir(piq)$_3$, Btp$_2$Ir(acac), DCJTB, and the like, but is not limited thereto.

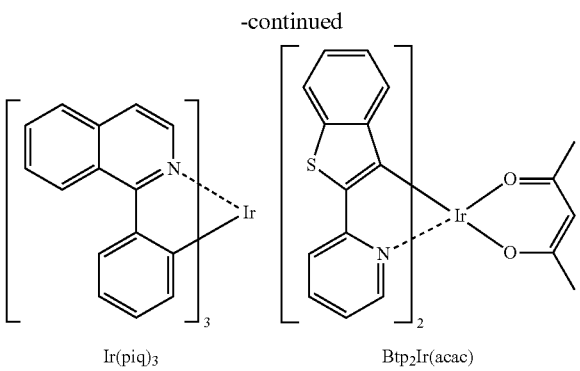

Ir(piq)$_3$     Btp$_2$Ir(acac)

A green dopant may include Ir(ppy)$_3$ (ppy=phenylpyridine), Ir(ppy)$_2$(acac), Ir(mpyp)$_3$, C545T, and the like, but is not limited thereto.

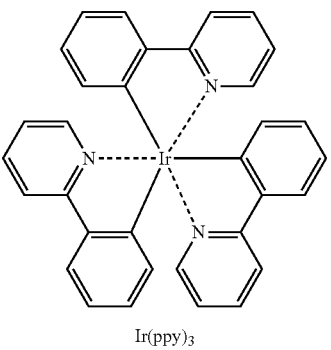

Ir(ppy)$_3$

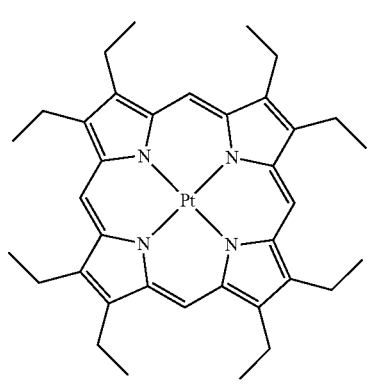

PtOEP

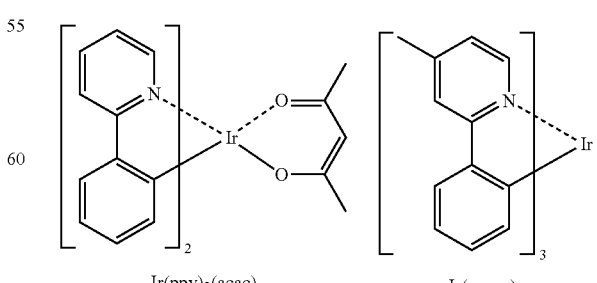

Ir(ppy)$_2$(acac)     Ir(mpyp)$_3$

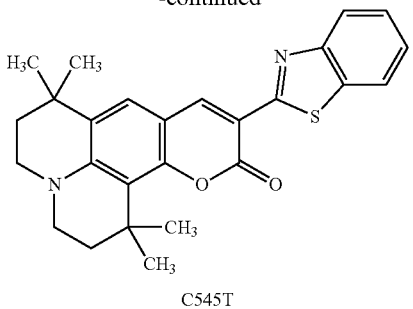

C545T

A blue dopant may include $F_2Irpic$, $(F_2ppy)_2Ir(tmd)$, Ir(dfppz)$_3$, ter-fluorene, 4,4'-bis(4-diphenylaminostyryl)biphenyl (DPAVBi), 2,5,8,11-tetra-ter-butyl perylene (TBP), and the like, but is not limited thereto.

The emission layer 5 may emit white by a combination of red, green and blue three primary colors, and the combination of colors may be implemented by combination of adjacent sub-pixels to emit white or stack in a vertical direction to emit white.

The electron auxiliary layer 4 may be interposed between the emission layer 5 and cathode 2 to increase electron mobility. The electron auxiliary layer 4 may include at least one selected from, for example an electron injection layer (EIL), an electron transport layer (ETL), and a hole blocking layer.

The electron auxiliary layer 4 may include the above-described organic compound. When the electron auxiliary layer 4 includes the above-described organic compound, the emission layer 5 may include, for example anthracene, arylamine, styrene, a derivative thereof, or a combination thereof.

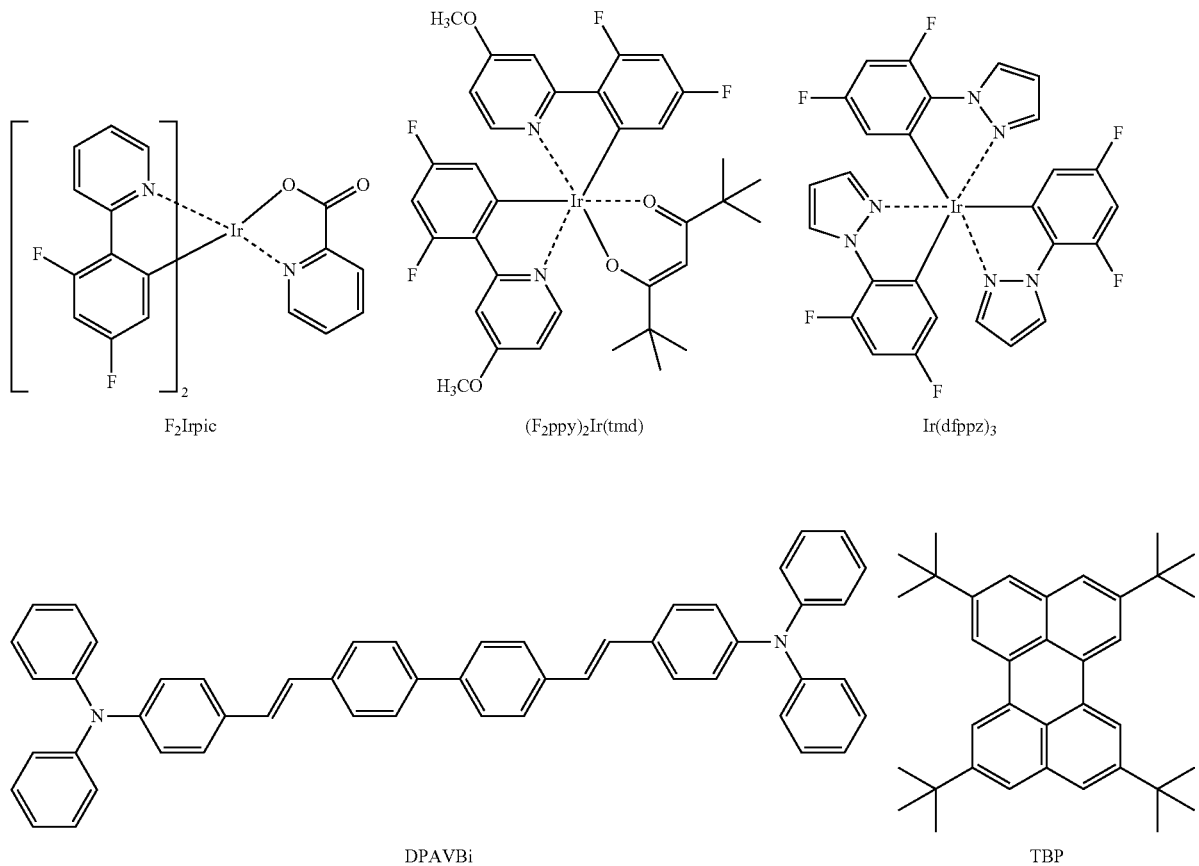

The dopant may be included in an amount of about 0.1 to about 15 parts by weight based on 100 parts by weight of emission layer forming material (i.e., total weight of the host and dopant is 100 parts by weight), without limitation.

The emission layer 5 may further include anthracene, arylamine, styrene, a derivative thereof, or a combination thereof as well as the above-described organic compound.

At least one hydrogen atom of the anthracene compound, arylamine compound or styrene compound may be substituted with the same substituent as that of the $C_1$ to $C_{30}$ alkyl group. The arylamine may be a $C_5$ to $C_{30}$ arylamine group, and may include an amino group substituted with a $C_6$ to $C_{30}$ aryl group or a $C_2$ to $C_{30}$ heteroaryl group.

The hole blocking layer material is not particularly limited, and may include any general hole blocking layer materials. For example, an oxadiazole derivative, a triazole derivative, a phenanthroline derivative, Balq, BCP, and the like may be used.

The electron transport layer (ETL) material may be the organic compound represented by Chemical Formula 1 as above-described. Any general electron transport layer (ETL) forming material may be also used. For example, a quinoline derivative, particularly well-known material such as tris(8-quinolinolate)aluminum Alq$_3$, TAZ, Balq, and the like may be used, without limitation.

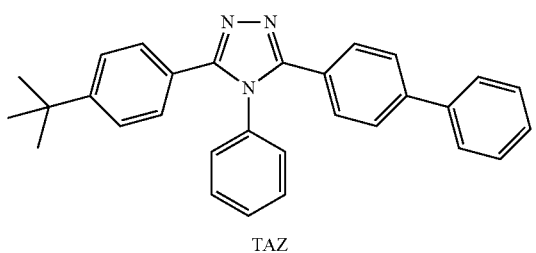

TAZ

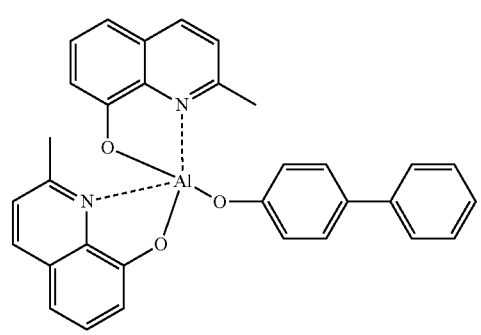

BAlq

An electron transport layer (ETL) of an organic light emitting diode device according to another embodiment may include an electron transport organic compound and a metal-containing material. Non-limiting examples of the electron transport organic compound may include DNA (9,10-di(naphthalen-2-yl)anthracene); and an anthracene-based compound such as the following compounds 101 and 102, but are not limited thereto.

Compound 101

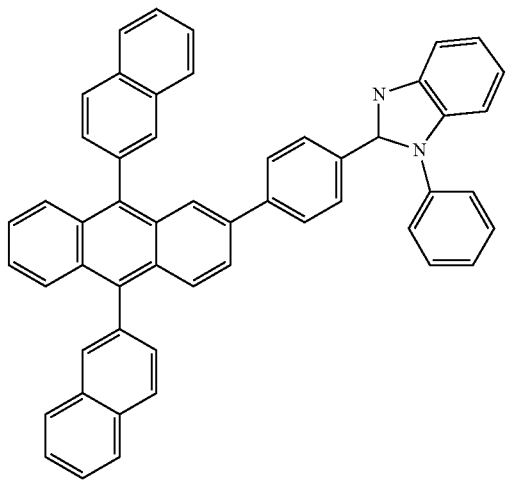

Compound 102

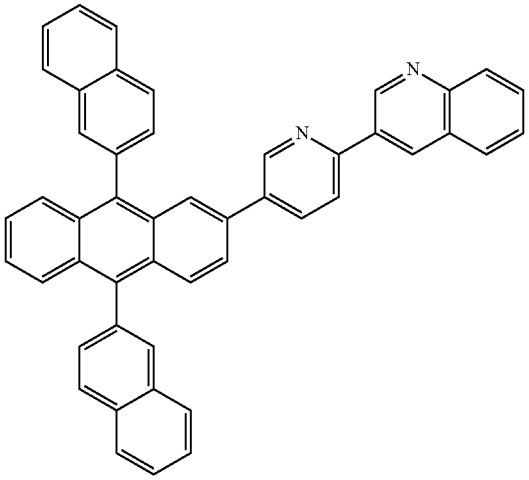

The metal-containing material may include a Li complex. Non-limiting examples of the Li complex may be lithium quinolate (LiQ) or the following compound 103, but are not limited thereto.

Compound 103

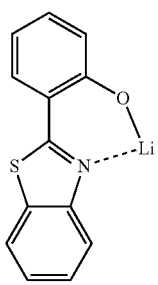

The hole auxiliary layer 3 may be interposed between the emission layer 5 and anode 1 to increase hole mobility. The hole auxiliary layer 3 may include, for example at least one layer selected from a hole injection layer (HIL), a hole transport layer (HTL), and an electron blocking layer.

The hole injection layer (HIL) may include general hole injection material, for example, a phthalocyanine compound such as copper-phthalocyanine, and the like, m-MTDATA [4,4',4''-tris(3-methylphenylphenylamino)triphenylamine], NPB (N,N'-di(1-naphthyl)-N,N'-diphenylbenzidine, TDATA, 2T-NATA, Pani/DBSA (polyaniline/dodecylbenzenesulfonic acid), PEDOT/PSS (poly(3,4-ethylenedioxythiophene)/poly(4-styrenesulfonate)), pani/CSA (polyaniline/camphor sulfonic acid) or PANI/PSS (polyaniline)/poly(4-styrenesulfonate)), and the like, but is not limited thereto.

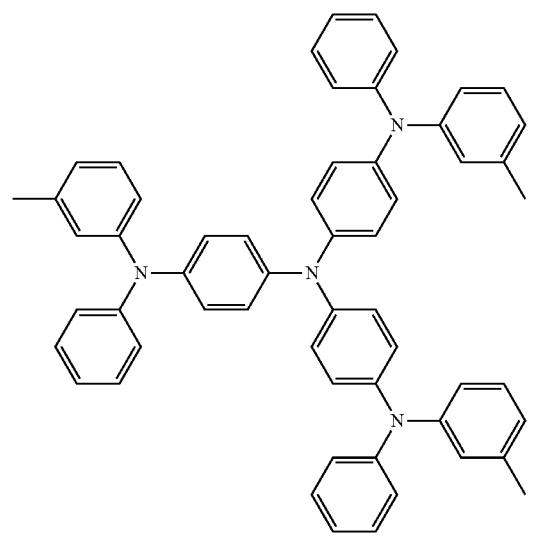

m-MTDATA

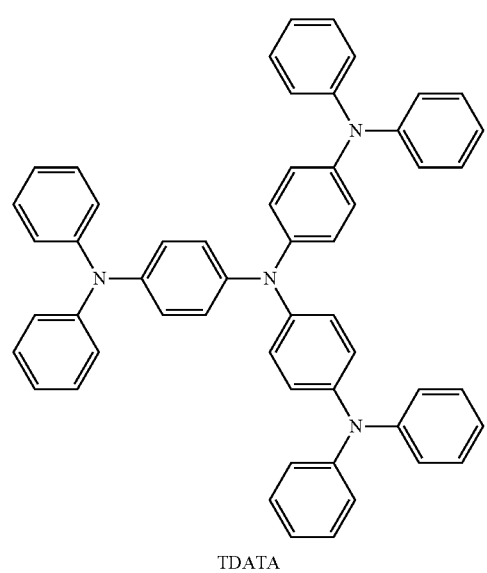

TDATA

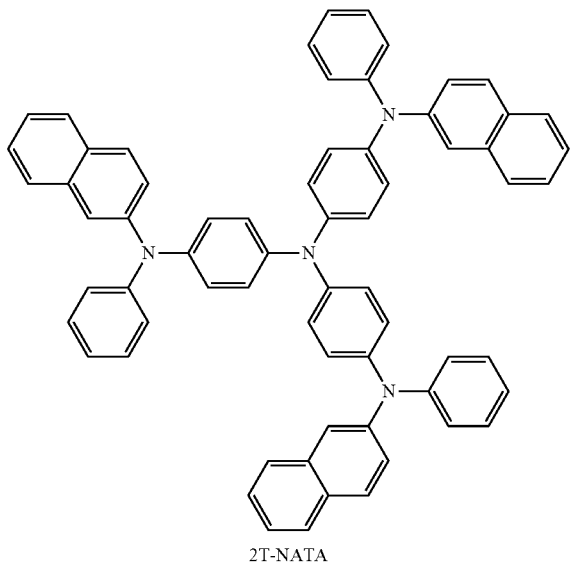

2T-NATA

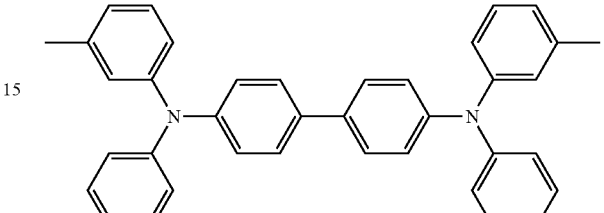

TPD

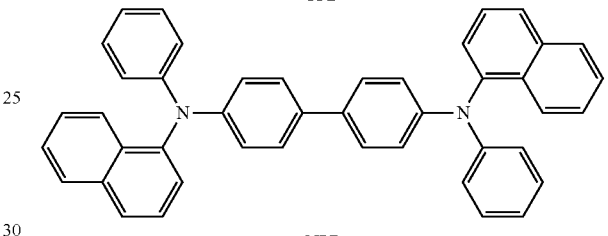

NPB

The hole transport layer (HTL) may include a general hole transport layer (HTL) material, for example, a carbazole derivative such as N-phenylcarbazole, polyvinylcarbazole, and the like, an amine derivative having an aromatic condensed ring such as NPB, N,N'-bis(3-methylphenyl)-N, N'-diphenyl-[1,1-biphenyl]-4,4'-diamine (TPD), and the like. For example, in the case of TCTA, it may prevent the diffusion of excitons from the emission layer as well as it may transport a hole.

The hole injection layer (HIL) or the hole transport layer (HTL) may further include a charge-generating material so as to improve film conductivity.

The charge-generating material may be for example, a p-dopant. Non-limiting examples of the p-dopant may include a quinone derivative such as tetracyanoquinone dimethane (TCNQ) and 2,3,5,6-tetrafluoro-tetracyano-1,4-benzoquinonedimethane (F4TCNQ); a metal oxide such as tungsten oxide and molybdenum oxide; and a cyano group-contained compound such as the following compound 100 or the like, but are not limited thereto.

Compound 100

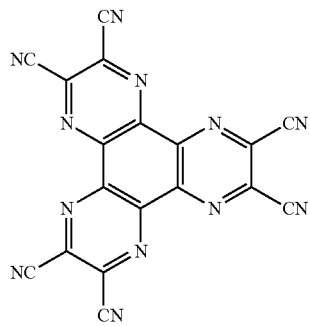

When the hole injection layer (HIL) or the hole transport layer (HTL) further include the charge-generating material, the charge-generating material may be variously modified such as uniformly dispersed in the layers or randomly distributed in the layers.

For example, an organic light emitting diode device according to one embodiment may have a structure of anode/hole injection layer (HIL)/emission layer/cathode, anode/hole injection layer (HIL)/hole transport layer (HTL)/ emission layer/electron transport layer (ETL)/cathode, or anode/hole injection layer (HIL)/hole transport layer (HTL)/ emission layer/electron transport layer (ETL)/electron injection layer (EIL)/cathode. In addition, the organic light emitting diode device may have a structure of anode/functional layer simultaneously having hole injection function and hole transport function/emission layer/electron transport layer (ETL)/cathode or anode/functional layer simultaneously having a hole injection function and a hole transport function/emission layer/electron transport layer (ETL)/electron injection layer (EIL)/cathode. Alternatively, the organic light emitting diode device may have a structure of anode/hole transport layer (HTL)/emission layer/functional layer simultaneously having electron injection function and electron transport function/cathode, anode/hole injection layer (HIL)/emission layer/functional layer simultaneously having electron injection function and electron transport function/cathode, or anode/hole injection layer (HIL)/hole transport layer (HTL)/emission layer/functional layer simultaneously having electron injection function and electron transport function/cathode structure, but is not limited thereto.

The organic layer 10 may be formed by, for example, various methods such as vacuum deposition, a spin coating, a casting, LB or the like.

When the organic layer is formed by the vacuum deposition, the deposition conditions may be different according to the compound used as the material for the organic layer, the structure of the desired organic layer, and thermal characteristics, but generally, may be appropriately selected within the ranges of deposit temperature of about 100 to about 500° C., the vacuum degree of about $10^{-8}$ to about $10^{-3}$ torr, and the deposition rate of about 0.01 to about 100 Å/sec, without limitation.

When the organic layer is formed by the spin coating, the coating conditions are different according to the compound used as a material for the organic layer, the structure of the desired organic layer, and thermal characteristics or the like, but may be suitably selected from the ranges of a coating speed of about 2000 rpm to about 5000 rpm, a heat treatment temperature of about 80° C. to about 200° C. for removing the solvent after coating, without limitation.

The organic layer 10 includes a layer including the organic compound represented by the above Chemical Formula 1, and the layer may be an emission layer.

The organic layer 10 may further include at least one layer of a hole injection layer (HIL), a hole transport layer (HTL), an electron blocking layer, a hole blocking layer, an electron transport layer (ETL), and an electron injection layer (EIL) as well as the emission layer.

The organic light emitting diode device may be electrically connected to for example a thin film transistor, and the thin film transistor may be disposed between the substrate and electrode.

In addition, the layer of organic light emitting diode device according to another embodiment may be formed by the deposition using the organic compound according to one embodiment or may be also formed by the wet method of coating the organic compound according to one embodiment in a solution.

Hereinafter, specific synthesis examples and examples illustrate these embodiments in more detail. However, the present disclosure is not limited to these embodiments.

SYNTHESIS EXAMPLES

Synthesis Example 1

Synthesis of Chemical Formula 3

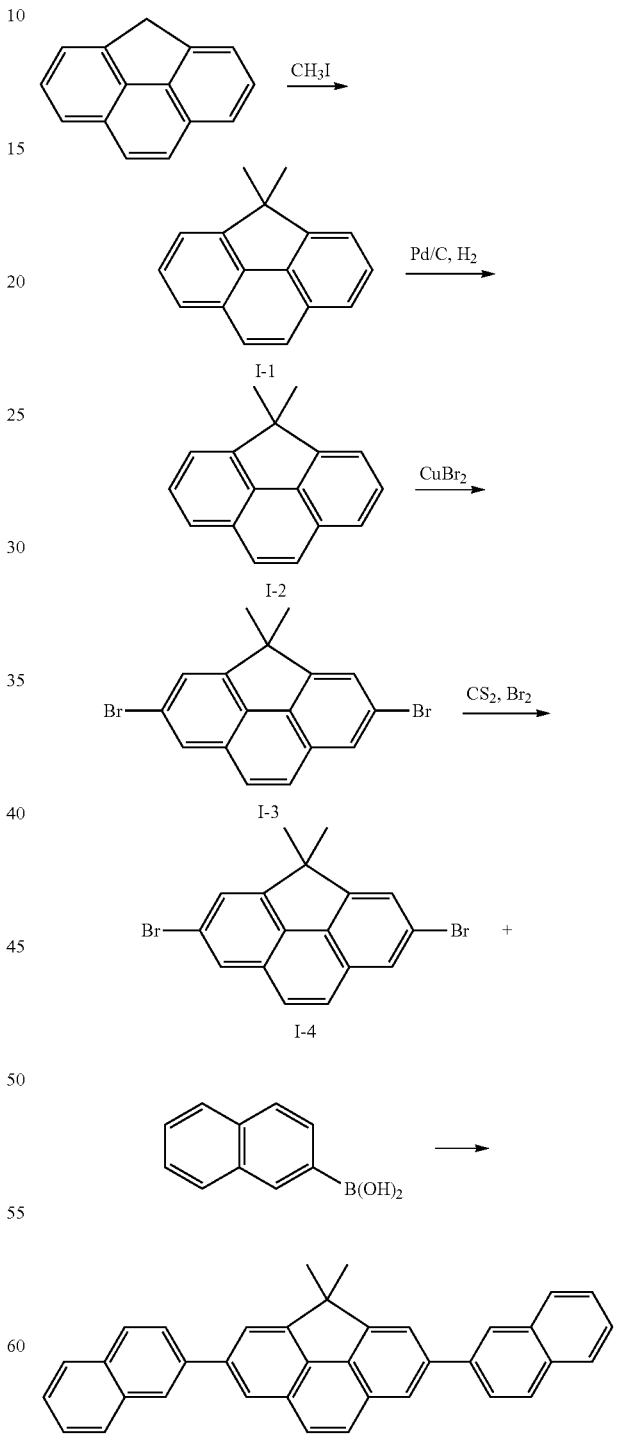

Chemical Formula 3

Synthesis of Intermediate I-1

3.80 g (20 mmol) of 4H-cyclopenta[def]phenanthrene was put in 20 mL of DMSO and 20 mL of a 50% sodium hydroxide aqueous solution, and 2.96 g (21 mmol) of iodomethane was slowly added thereto. The mixture was reacted at room temperature for 24 hours and three times extracted with 50 mL of water and 50 mL of diethylether. The obtained organic layer was dried with magnesium sulfate, a solvent therein was evaporated, and the obtained residues were separated and purified through silica gel column chromatography, obtaining 3.70 g of an intermediate I-1 (a yield of 85%). The produced compound was identified through MS/FAB. $C_{17}H_{14}$ (a calculation value: 218.11 g/mol, and a measurement value: 218.15 g/mol)

Synthesis of Intermediate I-2

3.70 g (17.0 mmol) of the intermediate I-1 and 600 mg of 10% palladium charcoal were dissolved in 100 mL of methanol/methylenechloride (1/1 of a volume ratio), and the solution was agitated under a hydrogen pressure (60 psi) for 15 hours. The agitated solution was filtered to remove a catalyst, a solvent therein was evaporated and removed, and the obtained residues were separated and purified through silica gel column chromatography, obtaining 3.52 g of an intermediate I-2 (a yield of 94%). The produced compound was identified through MS/FAB. $C_{17}H_{16}$ (a calculation value: 220.13 g/mol, and a measurement value: 220.10 g/mol)

Synthesis of Intermediate I-3

20 g of $CuBr_2$ was dissolved in 60 mL of distilled water, and 40 g of neutralized alumina was added to this aqueous solution at room temperature. Then, a solvent therein was evaporated, and the obtained residue was treated under a condition of 100° C., 4 Torr for 15 hours, obtaining $CuBr_2$ absorbed in the alumina. 1.54 g (7.00 mmol) of the intermediate I-2 was dissolved in 140 mL of carbon tetrachloride, and 62 g of the $CuBr_2$ was added thereto at room temperature. The mixture was agitated at 60° C. for 12 hours and filtered, and the obtained solid was cleaned with 60 mL of carbon tetrachloride. The obtained residue was separated and purified through silica gel column chromatography, obtaining 2.14 g of an intermediate I-3 (a yield of 81%). The produced compound was identified through MS/FAB. $C_{17}H_{14}Br_2$ (a calculation value: 375.95 g/mol, and a measurement value: 376.01 g/mol)

Synthesis of Intermediate I-4

2.14 g (5.66 mmol) of the intermediate I-3 was dissolved in 70 mL of $CS_2$, and another solution prepared by dissolving 0.32 mL (6.22 mmol) of bromine in $CS_2$ was slowly added in a dropwise fashion for 3 hours. The mixed solution was agitated for one hour and concentrated under vacuum for one hour, and the obtained residue was separated and purified through silica gel column chromatography, obtaining 1.92 g of an intermediate I-4 (a yield of 90%). The produced compound was identified through MS/FAB. $C_{17}H_{12}Br_2$ (a calculation value: 373.93 g/mol, and a measurement value: 373.96 g/mol)

Synthesis of Chemical Formula 3

1.92 g (5.10 mmol) of the intermediate I-4, 1.76 g (10.2 mmol) of naphthalene-2-boronic acid, 0.29 g (0.25 mmol) of $Pd(PPh_3)_4$(tetrakis(triphenylphosphine)palladium), 1.05 g (7.62 mmol) of $K_2CO_3$ were dissolved in 60 mL of a solution prepared by mixing $THF/H_2O$ in a volume ratio of 2/1), and the obtained solution was agitated at 70° C. for 10 hours. The reaction solution was cooled down to room temperature, 40 mL of water was added thereto, and the mixture was three times extracted with 40 mL of ethylether. The obtained organic layer was dried with magnesium sulfate, and a residue obtained by evaporating a solvent therein was separated and purified through silica gel column chromatography, obtaining 1.79 g of a compound represented by Chemical Formula 3 (a yield of 75%). The produced compound was identified through MS/FAB. $C_{37}H_{26}$ (a calculation value: 470.20 g/mol, and a measurement value: 470.25 g/mol)

Synthesis Example 2

Synthesis of Chemical Formula 5

2.24 g of a compound represented by Chemical Formula 5 (a yield of 71%) was obtained according to the same method as Synthesis Example 1 of preparing the compound represented by the above Chemical Formula 3 by using pyrene-1-boronic acid instead of naphthalene-2-boronic acid. The produced compound was identified through MS/FAB. $C_{49}H_{32}$ (a calculation value: 620.25 g/mol, and a measurement value: 620.20 g/mol)

Synthesis Example 3

Synthesis of Chemical Formula 13

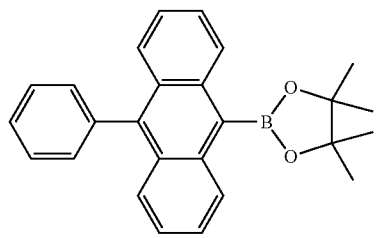

I-5

2.24 g of a compound represented by Chemical Formula 13 (a yield of 78%) was obtained according to the same method as Synthesis Example 1 of preparing the compound represented by the above Chemical Formula 3 by using the intermediate I-5 instead of naphthalene-2-boronic acid. The produced compound was identified through MS/FAB. $C_{57}H_{38}$ (a calculation value: 722.30 g/mol, and a measurement value: 722.28 g/mol)

Synthesis Example 4

Synthesis of Chemical Formula 35

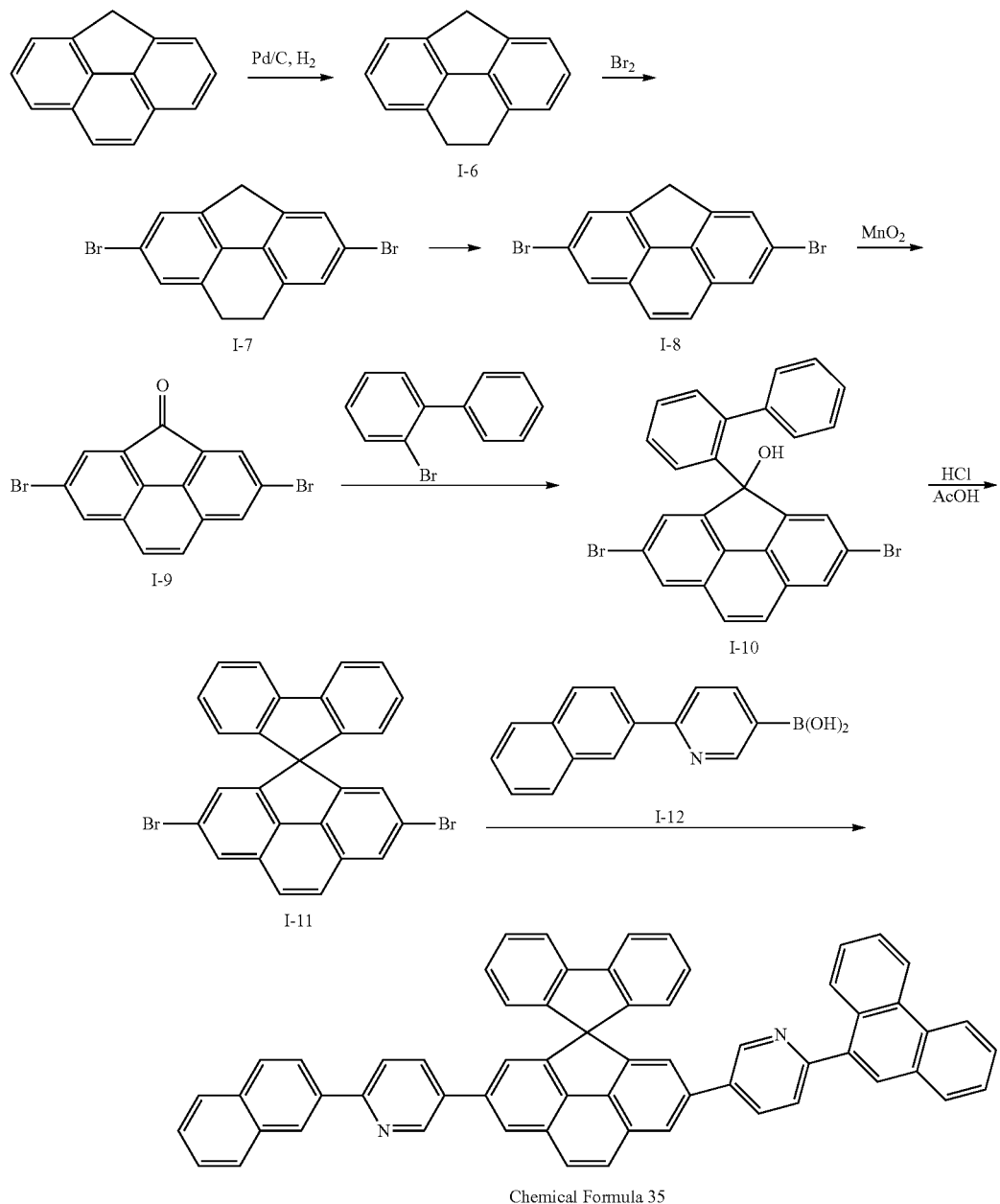

Chemical Formula 35

Synthesis of Intermediate I-6

10.0 g (52.6 mmol) of 4H-cyclopenta[def]phenanthrene and 8.40 g of 5% Pd/C were dissolved in 70 mL of EtOH in a Par reactor bottle, and the solution was agitated at room temperature for 24 hours, while its hydrogen pressure was maintained at 40 psi. When the reaction was complete, the reaction solution was filtered, and a solvent therein was evaporated, obtaining 8.60 g of an intermediate I-6 (a yield of 85%). The produced compound was identified through MS/FAB. $C_{15}H_{12}$ (a calculation value: 192.09 g/mol, and a measurement value: 192.11 g/mol)

Synthesis of Intermediate I-7

8.50 g (44.2 mmol) of the intermediate I-6 was dissolved in 80 mL of $CCl_4$, and 14.2 g (88.4 mmol) of $Br_2$ was slowly added thereto in a dropwise fashion at 0° C. The reaction solution was agitated at room temperature for 4 hours, and a 10% $Na_2SO_3$ solution was added thereto, obtaining an organic layer. The organic layer was dried with magnesium sulfate and then, recrystallized with n-hexane after evaporating a solvent therein, obtaining 8.9 g of an intermediate I-7 (a yield of 57%). The produced compound was identified through MS/FAB. $C_{15}H_{10}Br_2$ (a calculation value: 347.91 g/mol, and a measurement value: 347.88 g/mol)

Synthesis of Intermediate I-8

8.9 g (25.4 mmol) of the intermediate I-7 and 6.6 g (27.0 mmol) of o-chloranil were dissolved in 70 mL of Xylene, and the solution was agitated at 110° C. for 72 hours. The reaction solution was cooled down to room temperature, and a residue obtained by evaporating a solvent therein was separated and purified through silica gel column chromatography, obtaining 7.16 g of an intermediate I-8 (a yield of 81%). The produced compound was identified through MS/FAB. $C_{15}H_8Br_2$ (a calculation value: 345.90 g/mol, and a measurement value: 345.87 g/mol).

Synthesis of Intermediate I-9

7.16 g (20.6 mmol) of the intermediate I-8 and 280 g of $MnO_2$ were dissolved in 200 mL of benzene, and the solution was agitated at 80° C. for 20 hours. The reaction solution was cooled down to room temperature, filtered to remove $MnO_2$, and cleaned with $CHCl_3$ (50 mL), THF (50 mL), and MeOH (50 mL) in order. The filtered solution was evaporated, and the obtained residue was recrystallized with acetone, obtaining 3.73 g of an intermediate I-9 (a yield of 50%). The produced compound was identified through MS/FAB. $C_{15}H_6Br_2O$ (a calculation value: 359.88 g/mol, and a measurement value: 359.91 g/mol)

Synthesis of Intermediate I-10

2.40 g (10.3 mmol) of 2-bromo biphenyl was dissolved in 50 mL of THF, and 12.1 mL (20.6 mmol, 1.7M in pentane) of t-BuLi was slowly added thereto in a dropwise fashion at −78° C. The mixture was agitated for one hour at the same temperature, 3.73 g (10.3 mmol) of the intermediate I-9 was slowly added in a dropwise fashion for 30 minutes, and the reaction solution was agitated at −78° C. for 30 minutes and additionally agitated for 3 hours. Then, 40 mL of water was added to the reaction solution and three times extracted with 50 mL of ethylacetate. The organic layer was dried with magnesium sulfate, and a residue obtained by evaporating a solvent therefrom was separated and purified through silica gel column chromatography, obtaining a 4.66 g of an intermediate I-10 (a yield of 93%). The produced compound was identified through MS/FAB. $C_{27}H_{16}Br_2O$ (a calculation value: 513.96 g/mol, and a measurement value: 514.01 g/mol)

Synthesis of Intermediate I-11

4.66 g (9.03 mmol) of the intermediate I-10 was dissolved in 50 mL of acetic acid, 3 mL of concentrated hydrochloric acid was slowly added thereto in a dropwise fashion at 0° C., and the mixture was agitated for 2 hours. A white solid produced during the reaction was filtered and cleaned with acetic acid and ethanol, obtaining 4.05 g of an intermediate I-11 (a yield of 90%). The produced compound was identified through MS/FAB. $C_{27}H_{14}Br_2$ (a calculation value: 495.95 g/mol, and a measurement value: 496.01 g/mol)

Synthesis of Chemical Formula 35

2.51 g of a compound represented by Chemical Formula 35 (a yield of 66%) was obtained according to the same method as the synthesis example of preparing the compound 2 by using the intermediate I-11 instead of the intermediate I-4 and the intermediate I-12 instead of the naphthalene-2-boronic acid. The produced compound was identified through MS/FAB. $C_{57}H_{34}N_2$ (a calculation value: 746.27 g/mol, and a measurement value: 746.30 g/mol)

Synthesis Example 5

Synthesis of Chemical Formula 46

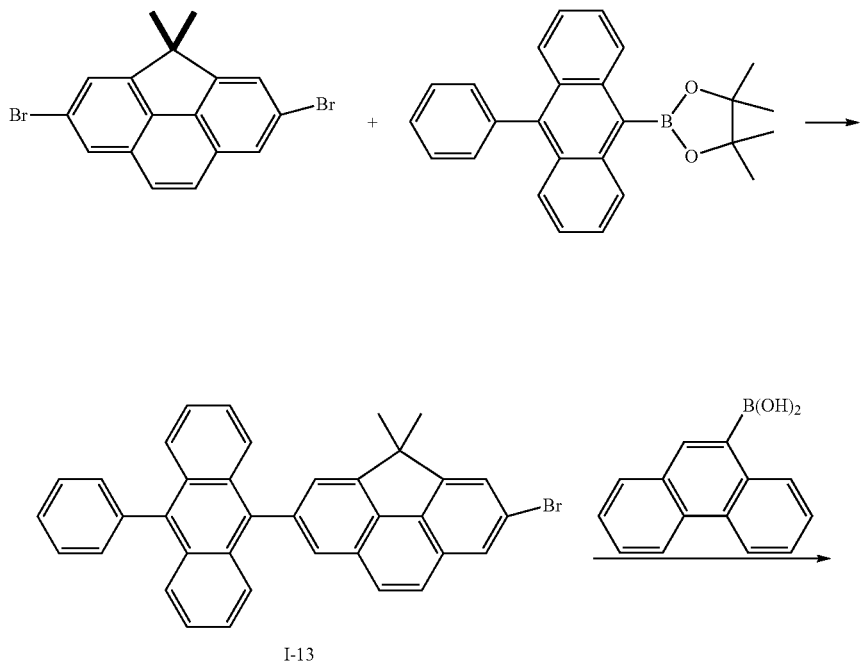

I-13

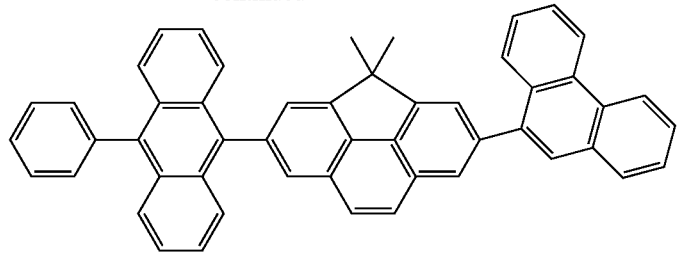

Chemical Formula 46

Synthesis of Intermediate I-13

5.49 g (14.6 mmol) of the intermediate I-4, 5.55 g (14.6 mmol) of the intermediate I-5, 0.84 g (0.73 mmol) of Pd(PPh$_3$)$_4$, and 6.05 g (43.8 mmol) of K$_2$CO$_3$ were dissolved in 60 mL of THF and 40 mL of H$_2$O, and the solution was agitated at 80° C. for 24 hours. The reaction solution was cooled down to room temperature, 50 mL of water was added thereto, and the mixture was three times extracted with 50 mL of ethylether. The organic layer was dried with magnesium sulfate, and a residue obtained by evaporating a solvent therein was separated and purified through silica gel column chromatography, obtaining 5.37 g of an intermediate I-13 (a yield of 67%). The produced compound was identified through MS/FAB. C$_{37}$H$_{25}$Br (a calculation value: 548.11 g/mol, a measurement value: 548.08 g/mol)

Synthesis of Chemical Formula 46

2.80 g (5.10 mmol) of the intermediate I-13, 1.13 g (5.10 mmol) of phenanthrene-9-boronic acid, 0.29 g (0.25 mmol) of Pd(PPh$_3$)$_4$, and 1.05 g (7.26 mmol) of K$_2$CO$_3$ were dissolved in 60 mL of THF and 40 mL of H$_2$O, and the solution was agitated at 80° C. for 24 hours. The reaction solution was cooled down to room temperature, 50 mL of water was added thereto, and the mixture was three times extracted with 50 mL of ethylether. The obtained organic layer was dried with magnesium sulfate, and a residue obtained by evaporating a solvent therein was separated and purified through silica gel column chromatography, obtaining 2.67 g of a compound represented by Chemical Formula 46 (a yield of 81%). The produced compound was identified through MS/FAB. C$_{51}$H$_{34}$ (a calculation value: 646.27 g/mol, and a measurement value: 646.30 g/mol)

Additional compounds were synthesized by using appropriate intermediate materials using the same synthesis method as the synthesis process, and the following Table 1 shows $^1$H NMR and MS/FAB of the compounds.

Other compounds than the compound in Table 1 may be easily synthesized with a reference to the aforementioned processes and raw materials by those who are skilled and knowledgeable in a related art.

TABLE 1

| Chemical Formula | $^1$H NMR (CDCl$_3$, 400 MHz) | MS/FAB Measurement value | MS/FAB Calculation value |
|---|---|---|---|
| 3 | d = 8.15-8.13 (m, 2H), 8.06-8.04 (m, 2H), 8.00-7.99 (m, 1H), 7.97-7.96 (m, 1H), 7.95-7.93 (m, 1H), 7.92-7.89 (m, 3H), 7.84-7.82 (m, 1H), 7.81-7.80 (m, 1H), 7.67-7.66 (m, 2H), 7.61-7.57 (m, 2H), 7.54-7.49 (m, 4H) 1.83 (s, 6H) | 470.25 | 470.20 |
| 5 | d = 8.16-8.14 (dd, 2H), 8.11-8.10 (m, 2H), 8.07-8.06 (m, 2H), 8.03-8.01 (m, 4H), 7.98-7.96 (m, 2H), 7.93-7.92 (m, 1H), 7.90-7.89 (m, 2H), 7.87-7.86 (m, 2H), 7.83 (s, 2H), 7.79 (s, 1H) 7.70-7.69 (m, 2H), 7.64 (d, 2H), 7.51-7.50 (m, 1H), 7.47-7.46 (m, 1H), 1.84 (s, 6H) | 620.20 | 620.25 |
| 7 | d = 8.20-8.19 (m, 2H), 8.11-8.10 (m, 2H), 8.00-7.98 (m, 2H), 7.96-7.93 (m, 2H), 7.87-7.84 (m, 4H), 7.64-7.59 (m, 2H), 7.56-7.52 (m, 2H), 7.44 (d, 2H), 7.42-7.41 (m, 2H) 7.36-7.30 (m, 4H), 7.20-7.14 (m, 6H) | 594.19 | 594.23 |
| 9 | d = 8.13-8.11 (dd, 2H), 8.06-8.04 (m, 2H), 7.93-7.91 (m, 1H), 7.90-7.88 (m, 1H), 7.87-7.86 (m, 2H), 7.84-7.82 (m, 2H), 7.77-7.74 (m, 2H), 7.73-7.70 (m, 4H) 7.66-7.64 (m, 2H), 7.63-7.59 (m, 6H), 7.55-7.51 (m, 4H), 1.83 (s, 6H) | 622.30 | 622.27 |
| 13 | d = 8.20-8.18 (m, 2H), 7.82-7.77 (m, 10H), 7.67 (d, 2H), 7.52-7.51 (dd, 2H), 7.50-7.45 (m, 6H), 7.41-7.39 (m, 3H), 7.38-7.37 dd, 2H), 7.36 (d, 1H), 7.32 (d, 1H), 7.30-7.29 (dd, 2H), 7.28 (d, 1H), 1.82 (s, 6H) | 722.28 | 722.30 |
| 19 | d = 8.13-8.11 (m, 4H), 7.93-7.92 (m, 1H), 7.91-7.90 (m, 1H), 7.85 (d, 1H), 7.83 (d, 1H), 7.73-7.71 (m, 1H), 7.70-7.69 (m, 1H), 7.67-7.64 (m, 4H), 7.55-7.52 (m, 2H), 7.42 (d, 2H), 7.35-7.31 (m, 2H), 1.84 (s, 6H) | 550.21 | 550.19 |
| 23 | d = 8.11-8.09 (m, 2H), 7.64-7.63 (m, 2H), 7.61-7.58 (m, 4H), 7.54-7.51 (m, 4H), 7.39 (d, 2H), 1.83 (s, 6H), 0.36 (s, 18H) | 514.22 | 514.25 |

TABLE 1-continued

| Chemical Formula | $^1$H NMR (CDCl$_3$, 400 MHz) | MS/FAB Measurement value | MS/FAB Calculation value |
|---|---|---|---|
| 26 | d = 8.21-8.20 (dd, 2H), 7.82-7.78 (m, 6H), 7.66 (d, 2H), 7.52-7.51 (dd, 2H), 7.50-7.49 (dd, 2H), 7.39 (d, 1H), 7.38 (d, 2H), 7.35 (d, 1H), 7.31-7.28 (m, 4H), 1.83 (s, 6H) | 732.38 | 732.36 |
| 30 | d = 8.21-8.19 (m, 2H), 8.13-8.12 (m, 2H), 8.06-8.05 (m, 2H), 7.99-7.97 (m, 2H), 7.96-7.94 (m, 2H), 7.83-7.82 (m, 1H), 7.81-7.80 (m, 1H), 7.71 (d, 1H), 7.69 (d, 1H), 7.67-7.66 (m, 2H), 7.63-7.60 (m, 4H), 7.52 (d, 2H), 7.49-7.46 (m, 3H), 7.45-7.44 (m, 1H), 7.42-7.39 (m, 2H), 1.84 (s, 6H) | 622.25 | 622.27 |
| 35 | d = 8.45 (d, 2H), 8.28-8.27 (m, 2H), 8.12-8.10 (dd, 2H), 8.04-8.03 (dd, 2H), 8.01-7.99 (m, 2H), 7.95-7.93 (m, 5H), 7.91-7.83 (m, 5H), 7.67 (s, 2H), 7.61-7.57 (m, 4H), 7.44 (t, 2H), 7.20 (t, 2H), 7.06 (d, 2H), 6.91-6.89 (dd, 2H) | 746.30 | 746.27 |
| 37 | d = 8.21-8.20 (m, 2H), 8.15-8.14 (m, 1H), 8.13-8.12 (m, 1H), 8.10-8.09 (m, 1H), 8.08-8.07 (m, 1H), 8.02-8.01 (m, 2H), 7.82 (d, 1H), 7.81-7.80 (m, 2H), 7.78-7.77 (m, 1H), 7.75-7.72 (m, 4H), 7.71-7.68 (m, 4H), 7.63-7.62 (m, 2H), 7.53 (d, 2H), 7.46-7.42 (m, 2H), 7.38-7.35 (m, 2H), 1.83 (s, 6H) | 734.20 | 734.21 |
| 40 | d = 8.24-8.22 (dd, 2H), 8.01-8.00 (m, 2H), 7.94-7.92 (m, 2H), 7.91-7.88 (m, 6H), 7.80-7.79 (m, 2H), 7.77-7.76 (dd, 2H), 7.75-7.74 (m, 2H), 7.65 (d, 2H), 7.62-7.60 (m, 2H), 7.59-7.55 (m, 6H), 7.40-7.34 (m, 8H) | 828.41 | 828.37 |
| 45 | d = 8.17-8.16 (dd, 2H), 8.07-8.06 (m, 2H), 7.94-7.93 (m, 1H), 7.92-7.91 (m, 1H), 7.87-7.85 (m, 3H), 7.83-7.81 (m, 3H), 7.71 (d, 1H), 7.69 (d, 1H), 7.67-7.66 (m, 2H), 7.62-7.58 (m, 2H), 7.55-7.47 (m, 8H), 7.20-7.17 (tt, 2H), 1.83 (s, 6H) | 622.25 | 622.27 |
| 46 | d = 8.27-8.25 (m, 1H), 8.20-8.18 (m, 1H), 8.13-8.12 (dd, 1H), 8.09-8.08 (dd, 1H), 7.82-7.77 (m, 7H), 7.70-7.69 (m, 1H), 7.67-7.63 (m, 4H), 7.54-7.46 (m, 6H), 7.41-7.36 (m, 3H), 7.32-7.28 (m, 2H), 7.18-7.14 (m, 1H), 1.84 (s, 6H) | 646.30 | 646.27 |
| 52 | d = 8.22-8.21 (m, 1H), 8.15-8.14 (m, 1H), 8.08-8.06 (m, 2H), 8.00-7.98 (m, 1H), 7.96-7.93 (m, 2H), 7.87-7.83 (m, 2H), 7.71-7.70 (m, 1H), 766-7.65 (m, 2H), 7.63-7.58 (m, 3H), 7.53-7.49 (m, 6H), 7.39-7.28 (m, 3H), 7.22-7.20 (m, 1H), 1.83 (s, 6H) | 585.23 | 585.25 |
| 58 | d = 8.45-8.44 (m, 2H), 8.31-8.29 (m, 2H), 8.20-8.18 (m, 2H), 8.07-8.04 (tt, 2H), 7.93-7.92 (m, 1H), 7.86-7.85 (m, 2H), 7.80-7.76 (m, 5H), 769-7.66 (m, 2H), 7.55-7.52 (m, 2H), 7.50-7.46 (m, 5H), 7.41-7.36 (m, 3H), 7.33-7.28 (m, 2H), 1.84 (s, 6H) | 700.31 | 700.29 |
| 60 | d = 8.49-8.47 (dd, 1H), 8.25-8.24 (m, 1H), 8.21-8.19 (dd, 1H), 8.14-8.12 (m, 2H), 8.07-8.06 (m, 1H), 8.01-7.99 (m, 1H), 7.94-7.90 (m, 5H), 7.76-7.74 (m, 3H), 7.66 (d, 1H), 7.62-7.58 (m, 4H), 7.56-7.52 (m, 2H), 7.47-7.44 (m, 1H), 7.40-7.33 (m, 4H), 1.83 (s, 6H) | 647.25 | 647.26 |
| 66 | d = 8.53-8.52 (dd, 1H), 8.42-8.40 (m, 5H), 8.33-8.31 (m, 1H), 8.24-8.22 (m, 1H), 8.17-8.15 (dd, 1H), 8.09-8.07 (m, 1H), 7.90-7.86 (m, 2H), 7.79-7.75 (m, 3H), 7.69-7.59 (m, 7H), 7.54-7.50 (m, 4H), 7.42-7.38 (m, 2H), 7.16-7.13 (m, 1H), 1.84 (s, 6H) | 701.30 | 701.28 |
| 70 | d = 8.52-8.51 (m, 2H), 8.44 (d, 1H), 8.40 (d, 1H), 8.32-8.30 (m, 2H), 8.23-8.20 (m, 2H), 8.17 (d, 1H), 8.13-8.12 (m, 1H), 8.09-8.08 (m, 1H), 8.05 (d, 2H), 7.98-7.89 (m, 5H), 7.82-7.80 (m, 1H), 7.71-7.69 (m, 1H), 7.62-7.60 (m, 2H), 7.50-7.41 (m, 7H), 7.25-7.22 (tt, 2H), 7.10-7.09 (m, 1H), 7.04-7.02 (dd, 2H) | 744.30 | 744.28 |

EXAMPLES

Example 1

15 Ω/cm² (1200 Å) ITO glass substrate (manufactured by Corning) was cut in a size of 50 mm×50 mm×0.7 mm and cleaned with ultrasonic wave using isopropyl alcohol and pure water for each 5 minutes, and then irradiated with ultraviolet (UV) for about 30 minutes and cleaned by exposing ozone. 2-TNATA was vacuum deposited on the ITO glass substrate to form a hole injection layer (HIL) having a thickness of 600 Å, and 4,4'-bis [N-(1-naphthyl)-N-phenylamino]biphenyl (hereinafter, NPB) was vacuum deposited to form a hole transport layer (HTL) having a thickness of 300 Å.

The following Chemical Formula 5 as a blue fluorescent host and 4,4'-bis [2-(4-(N,N-diphenylamino)phenyl)vinyl]biphenyl (hereinafter, DPAVBi) as a blue fluorescent dopant were co-deposited on the hole transport layer (HTL) in a weight ratio of 98:2 to form a 300 Å-thick emission layer.

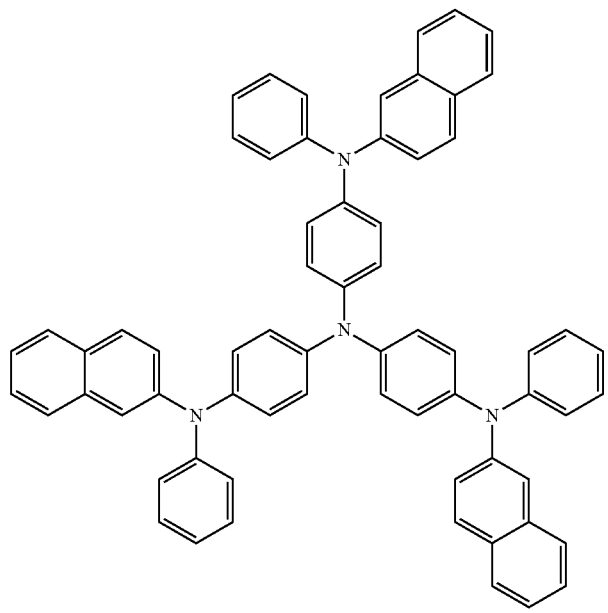

2-TNATA

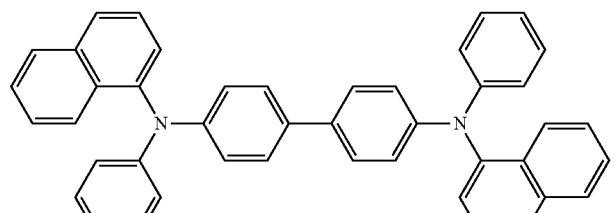

NPB

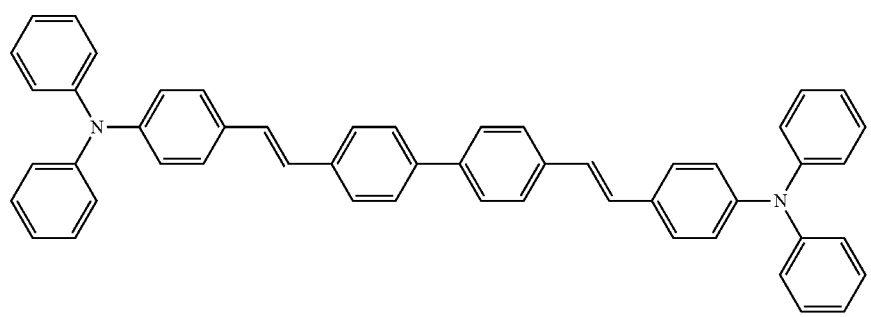

DPAVBi

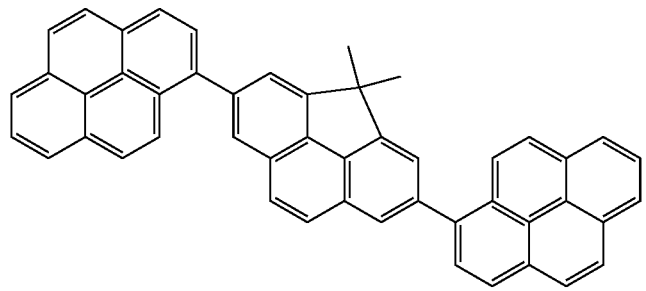

Then, Alq₃ was deposited on the emission layer in a thickness of 300 Å to form an electron transport layer (ETL) and LiF was deposited on the electron transport layer (ETL in a thickness of 10 Å to form an electron injection layer (EIL). Al was vacuum deposited on the electron injection layer (EIL) in a thickness of 3000 Å to form a cathode and thus organic light emitting diode device was manufactured.

Example 2

An organic light emitting diode device was manufactured in accordance with the same procedure as in Example 1, except using the following Chemical Formula 13 to form an emission layer, instead of the compound 4.

Chemical Formula 5

Chemical Formula 13

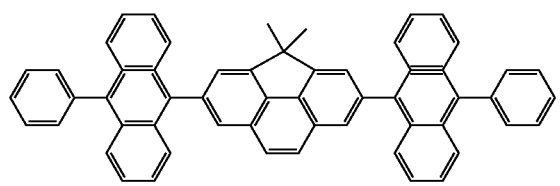

Example 3

An organic light emitting diode device was manufactured in accordance with the same procedure as in Example 1, except using the Chemical Formula 30 to form an emission layer, instead of the compound 4.

Chemical Formula 30

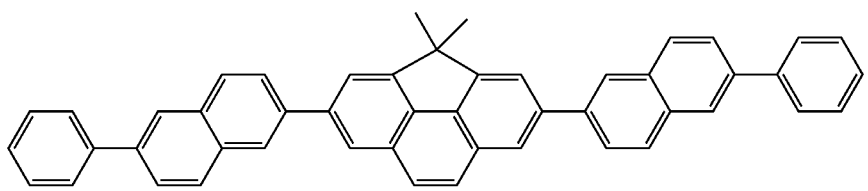

Example 4

An organic light emitting diode device was manufactured in accordance with the same procedure as in Example 1, except using the Chemical Formula 35 to form an emission layer, instead of the compound 4.

Chemical Formula 35

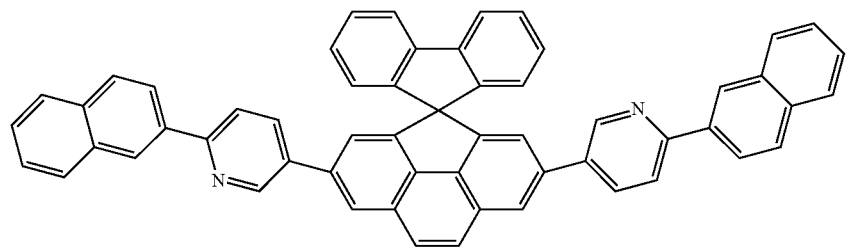

Example 5

An organic light emitting diode device was manufactured in accordance with the same procedure as in Example 1, except using the Chemical Formula 40 to form an emission layer, instead of the compound 4.

Chemical Formula 40

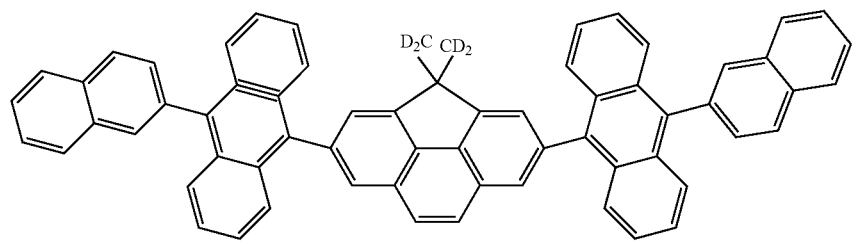

Example 6

An organic light emitting diode device was manufactured in accordance with the same procedure as in Example 1, except using the Chemical Formula 46 to form an emission layer, instead of the compound 4.

Chemical Formula 46

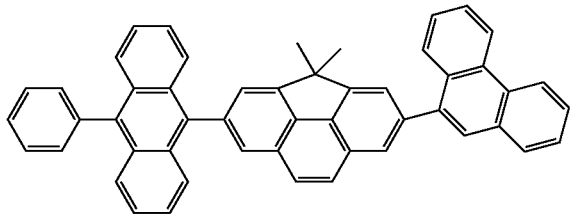

Example 7

An organic light emitting diode device was manufactured in accordance with the same procedure as in Example 1, except using 9,10-di-naphthalen-2-yl-anthracene (hereinafter, DNA) to form an emission layer, instead of the compound 4 and using the following Chemical Formula 58 to form an electron transport layer (ETL), instead of $Alq_3$.

Chemical Formula 58

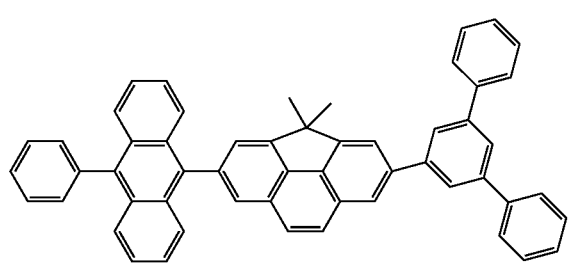

Example 8

An organic light emitting diode device was manufactured in accordance with the same procedure as in Example 7, except using the following Chemical Formula 66 to form an electron transport layer (ETL), instead of the compound 57.

Chemical Formula 66

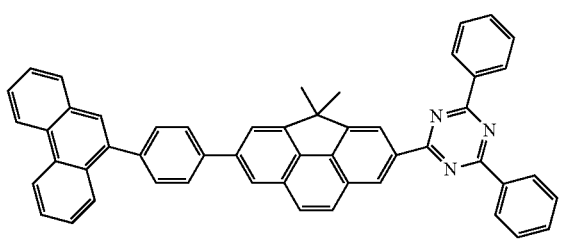

Comparative Example 1

An organic light emitting diode device was manufactured in accordance with the same procedure as in Example 1, except using a blue fluorescent host, DNA to form an emission layer, instead of the compound 4.

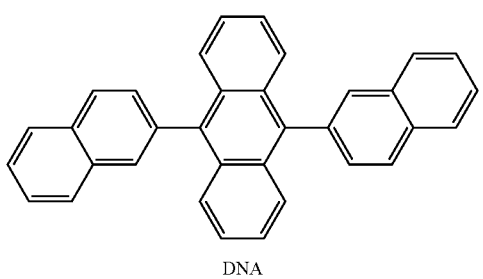 [SMILES: c1ccc2cc(-c3c4ccccc4c(-c4ccc5ccccc5c4)c4ccccc34)ccc2c1]

DNA

Evaluation

The characteristics of organic light emitting diode devices obtained from Examples 1 to 8 and Comparative Example 1 were evaluated.

The results are shown in Table 2.

TABLE 2

| | Light emitting material or electron transport material | Driving voltage (V) | Current density (mA/cm$^2$) | Luminance (cd/m$^2$) | Efficiency (cd/A) | Light emitting color | half life-span (hr @ 100 mA/cm$^2$) |
|---|---|---|---|---|---|---|---|
| Example 1 | Chemical Formula 5 | 6.36 | 50 | 3,205 | 6.41 | blue | 304 hr |
| Example 2 | Chemical Formula 13 | 6.23 | 50 | 3,175 | 6.35 | blue | 326 hr |
| Example 3 | Chemical Formula 30 | 6.25 | 50 | 3,145 | 6.29 | blue | 313 hr |
| Example 4 | Chemical Formula 35 | 6.46 | 50 | 3,035 | 6.07 | blue | 288 hr |
| Example 5 | Chemical Formula 40 | 6.19 | 50 | 3,165 | 6.33 | blue | 323 hr |
| Example 6 | Chemical Formula 46 | 6.17 | 50 | 3,115 | 6.23 | blue | 307 hr |
| Example 7 | Chemical Formula 58 | 5.17 | 50 | 3,235 | 6.47 | blue | 413 hr |
| Example 8 | Chemical Formula 66 | 5.25 | 50 | 3,315 | 6.63 | blue | 435 hr |
| Comparative Example 1 | DNA | 7.35 | 50 | 2,065 | 4.13 | blue | 145 hr |

Referring to Table 2, the organic light emitting diode devices according to Examples 1 to 8 showed all improved driving voltage, luminance, efficiency, and life-span characteristic compared with the organic light emitting diode device according to Comparative Example 1.

When the compounds according to Examples 1 to 8 were all applied as a host material of a blue emission layer and an electron transport material to an organic light emitting diode device, the compounds improved driving voltage and efficiency of the organic light emitting diode device compared with a conventional material, DNA and Alq$_3$ and realized excellent I-V-L characteristic and in particular, remarkably improved life-span.

While these embodiments have been described in connection with what is presently considered to be practical example embodiments, it is to be understood that the embodiments are not limited to the disclosed embodiments, but, on the contrary, is intended to cover various modifications and equivalent arrangements included within the spirit and scope of the appended claims. Therefore, the aforementioned embodiments should be understood to be examples but not limiting this disclosure in any way.

What is claimed is:

1. An organic compound comprising at least one selected from the compounds listed in the following Group 1:

Chemical Formula 2

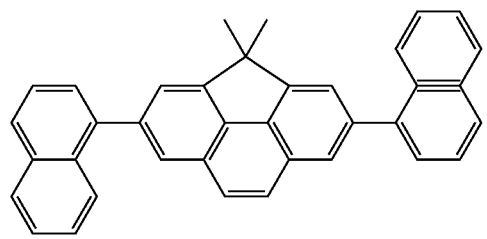

Chemical Formula 3

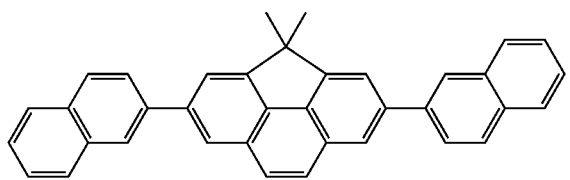

Chemical Formula 4

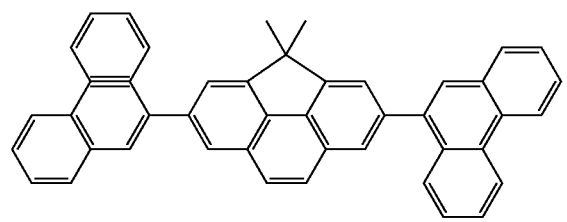

Chemical Formula 5

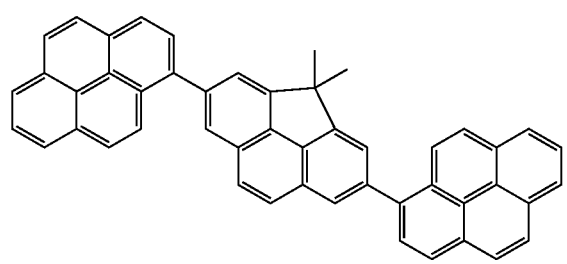

Chemical Formula 6

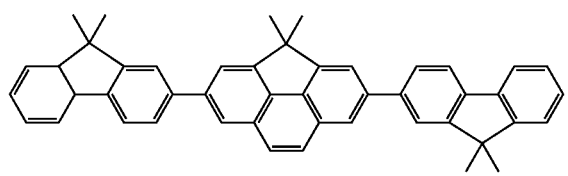

Chemical Formula 7
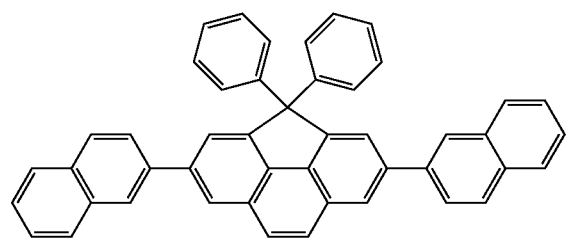
Chemical Formula 8
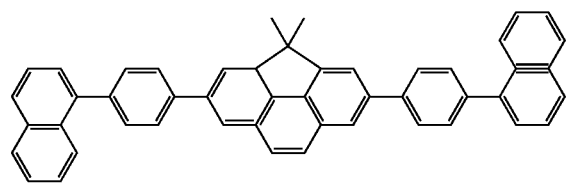
Chemical Formula 9
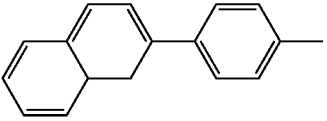
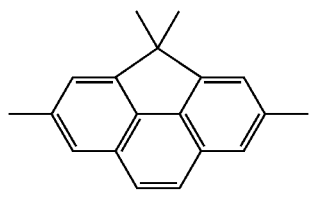
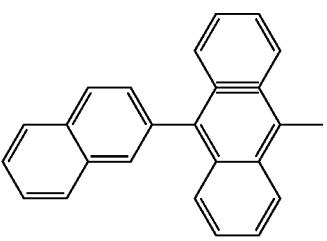
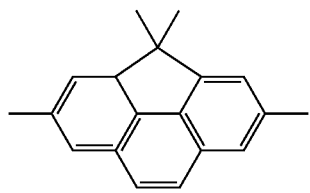
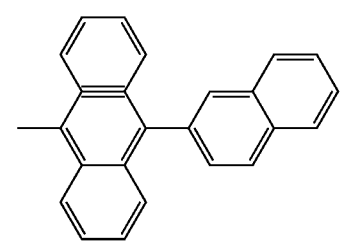
Chemical Formula 11
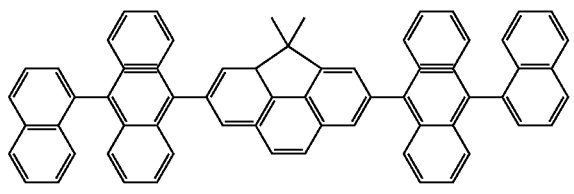
Chemical Formula 12
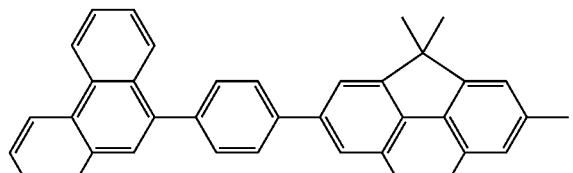
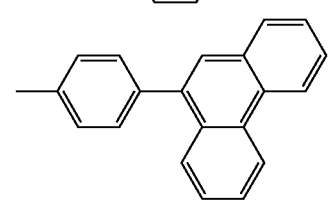
Chemical Formula 13
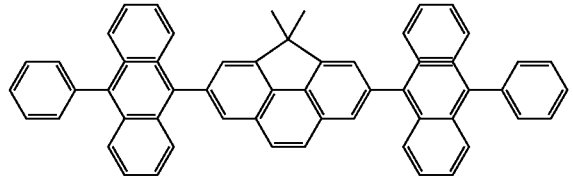
Chemical Formula 14
Chemical Formula 15
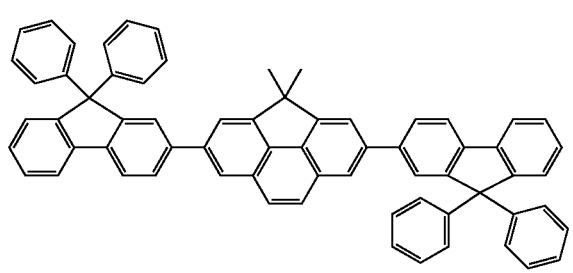

Chemical Formula 16
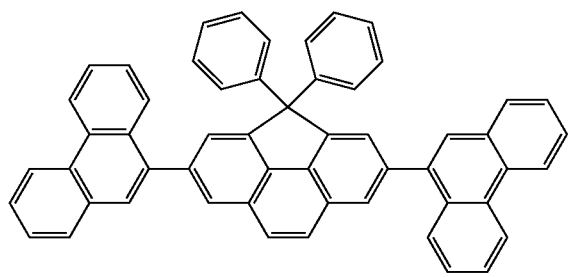
Chemical Formula 17
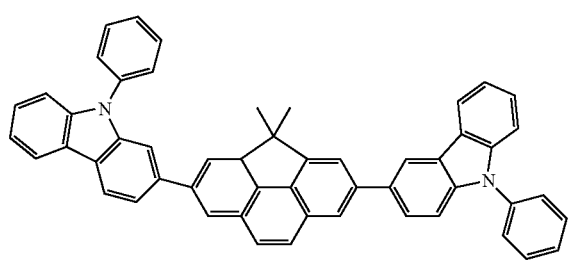
Chemical Formula 18
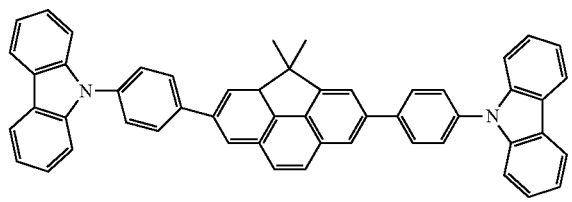
Chemical Formula 19
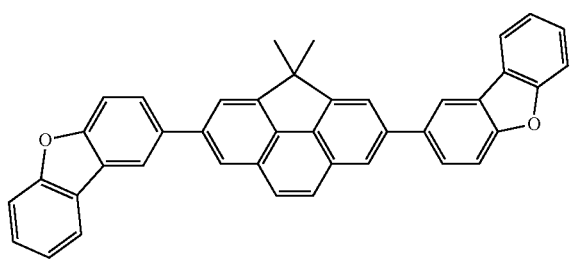
Chemical Formula 20
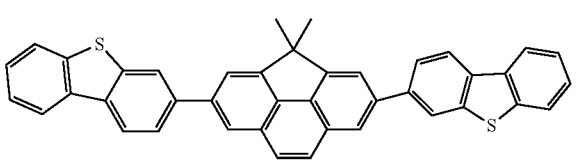
Chemical Formula 21
Chemical Formula 24
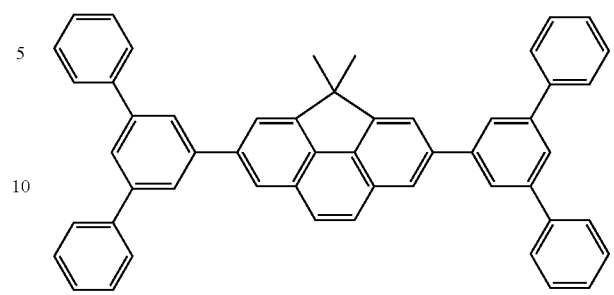
Chemical Formula 25
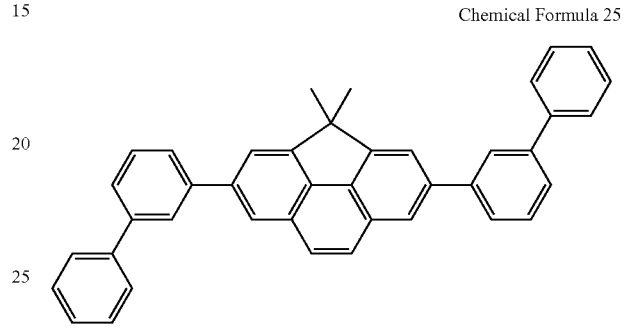
Chemical Formula 26
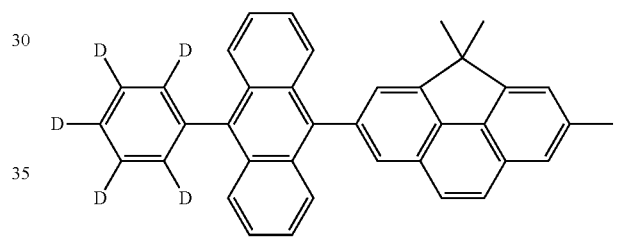
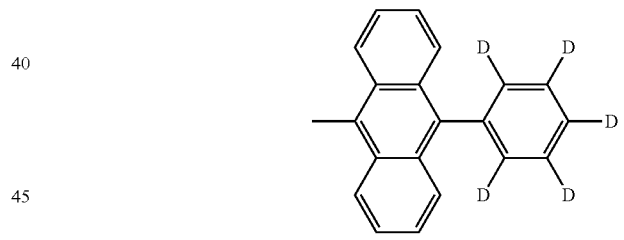
Chemical Formula 27
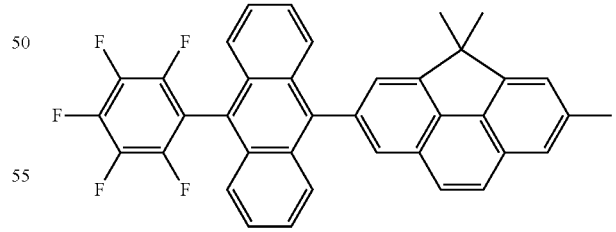
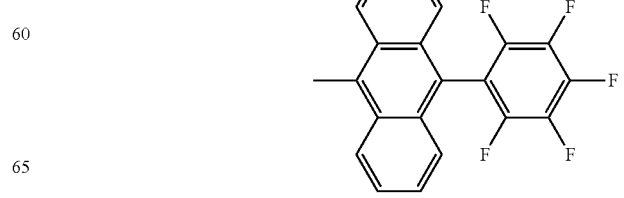

Chemical Formula 28
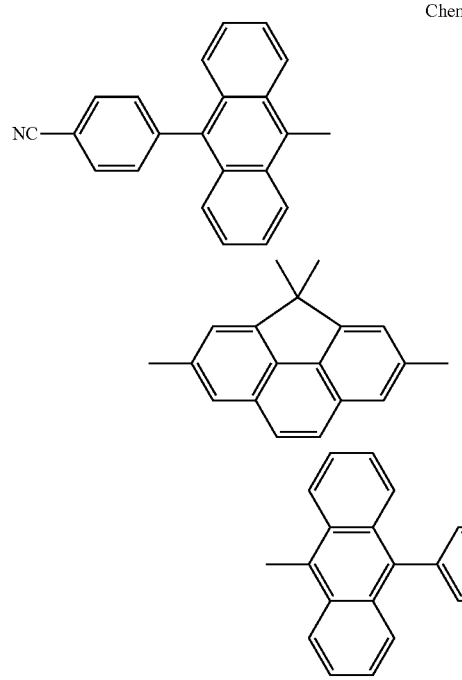
Chemical Formula 29
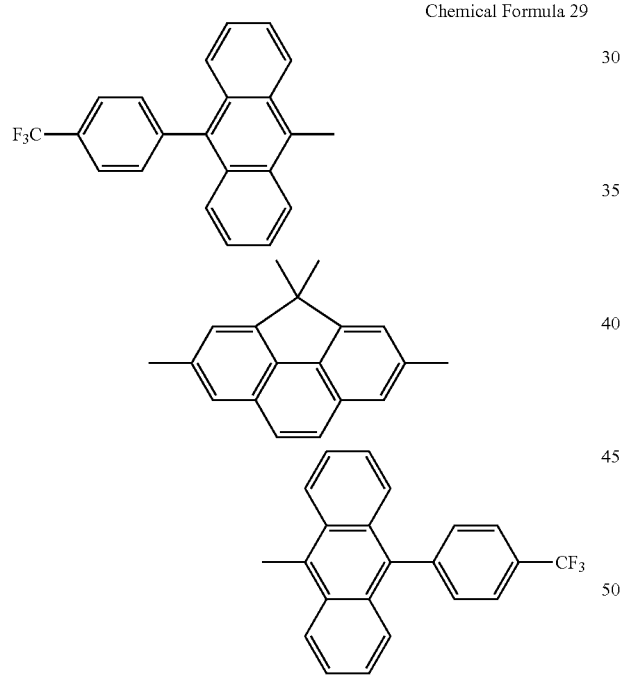
Chemical Formula 30
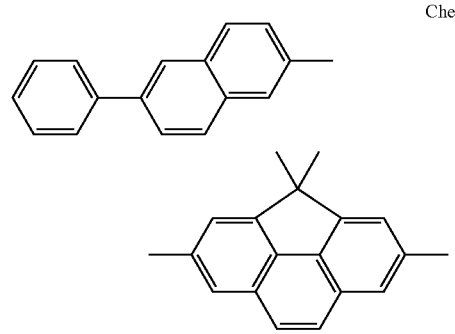
Chemical Formula 31
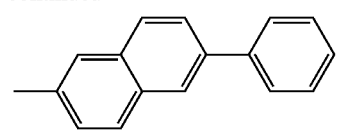
Chemical Formula 32
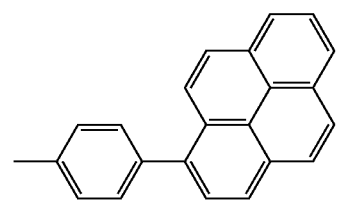
Chemical Formula 33
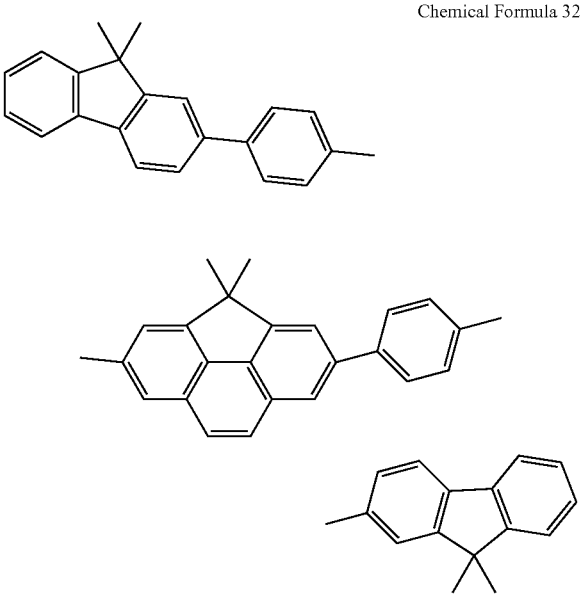

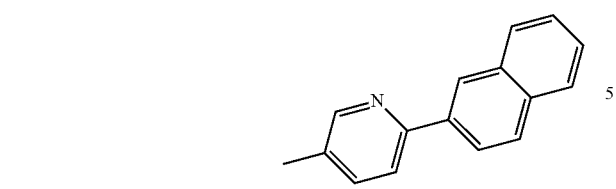
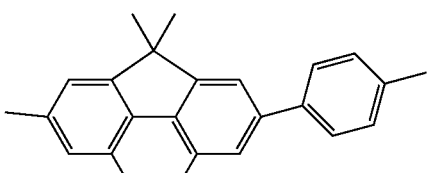
Chemical Formula 34
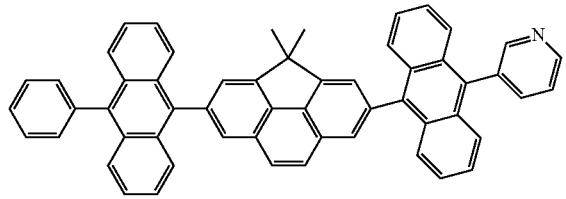
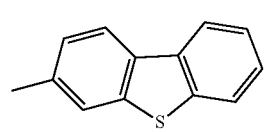
Chemical Formula 38
Chemical Formula 35
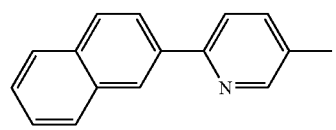
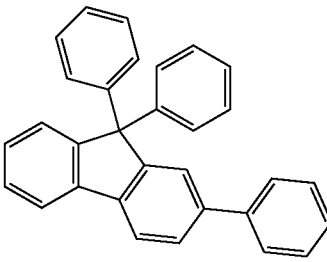
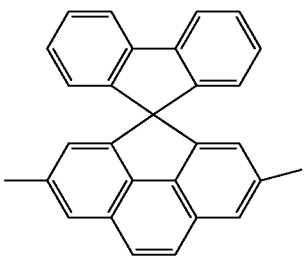
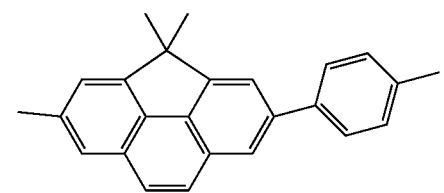
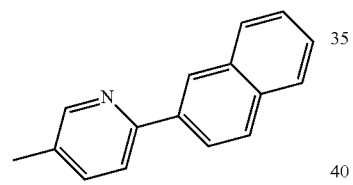
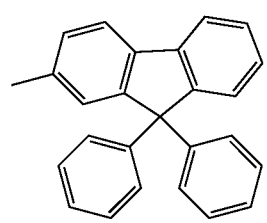
Chemical Formula 36
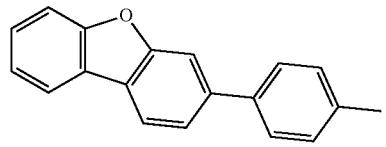
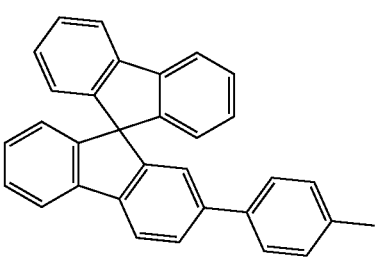
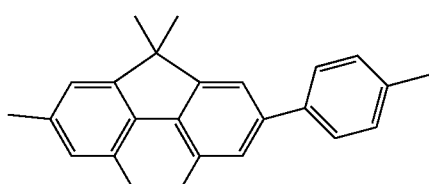
Chemical Formula 39
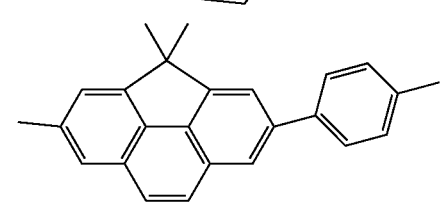
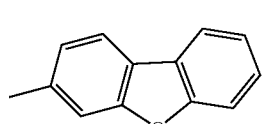
Chemical Formula 37
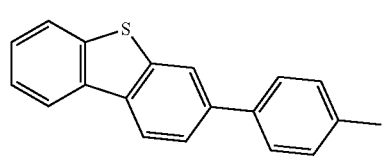
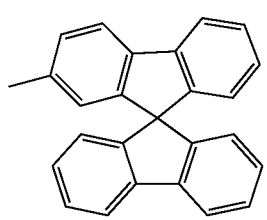

Chemical Formula 40
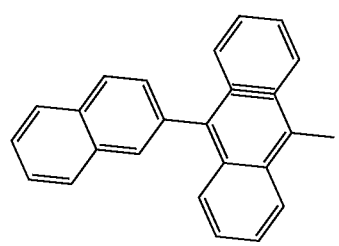
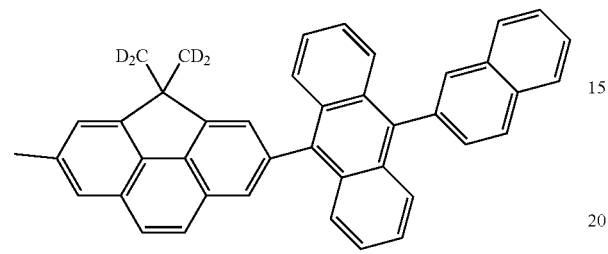
Chemical Formula 41
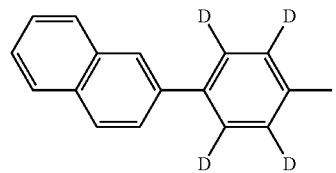
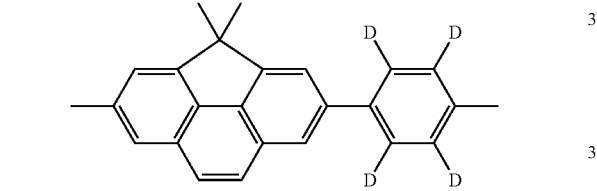
Chemical Formula 42
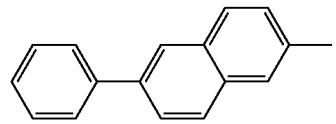
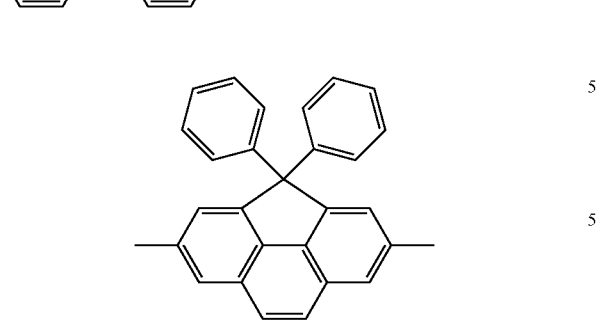
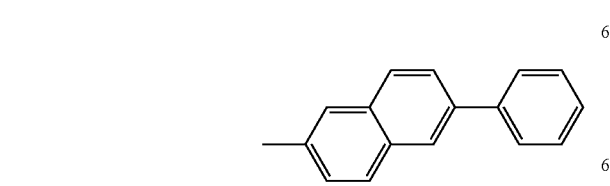
Chemical Formula 43
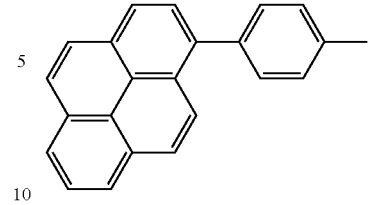
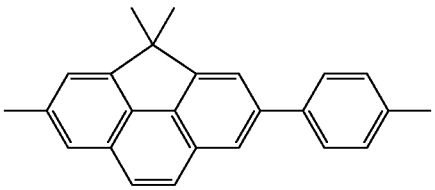
Chemical Formula 44
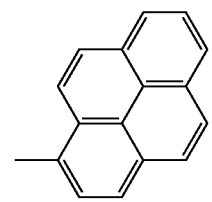
Chemical Formula 45
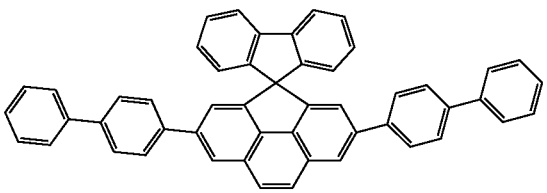
Chemical Formula 46
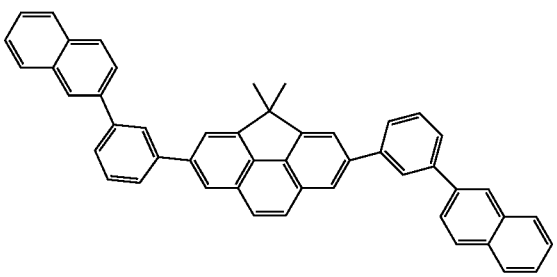
Chemical Formula 47
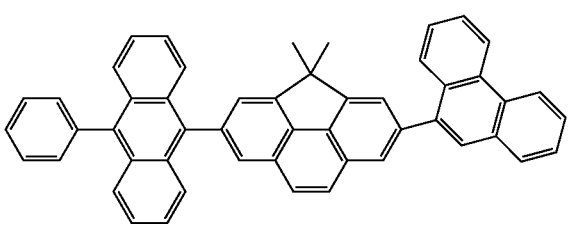
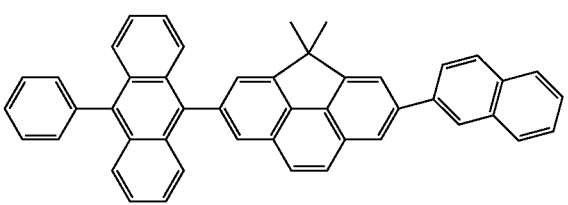

Chemical Formula 48
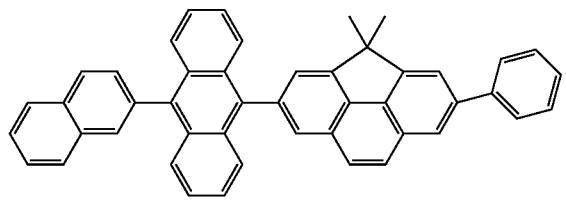
Chemical Formula 49
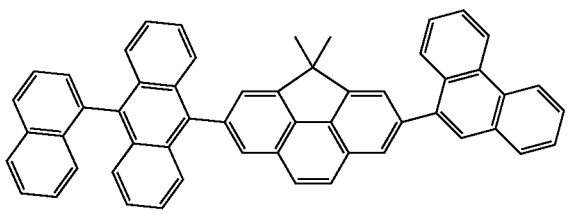
Chemical Formula 50
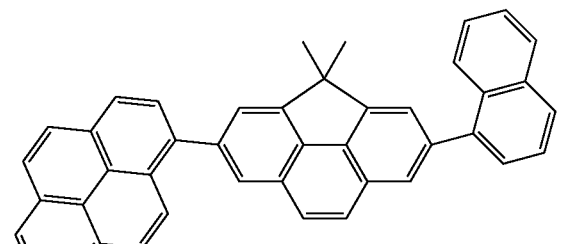
Chemical Formula 51
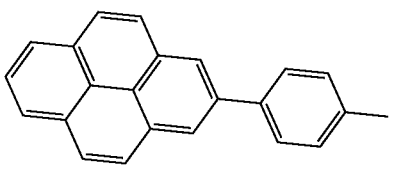
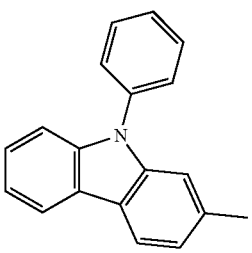
Chemical Formula 52
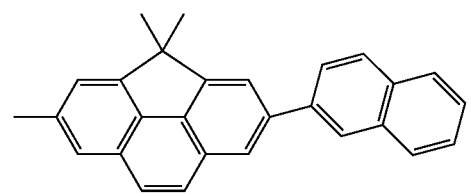
Chemical Formula 53
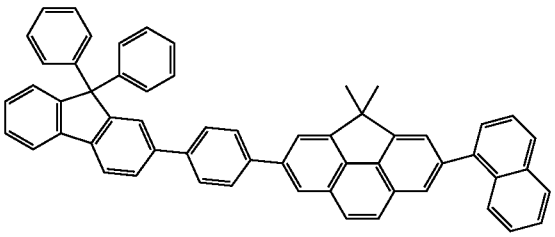
Chemical Formula 54
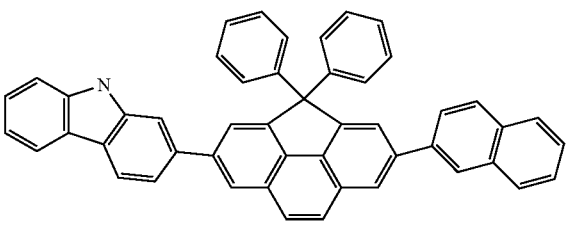
Chemical Formula 55
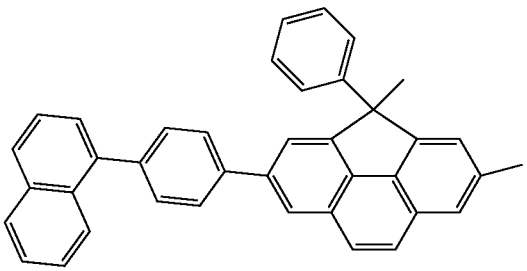
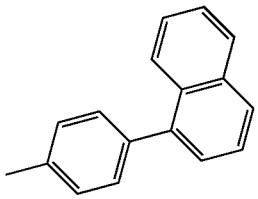
Chemical Formula 56
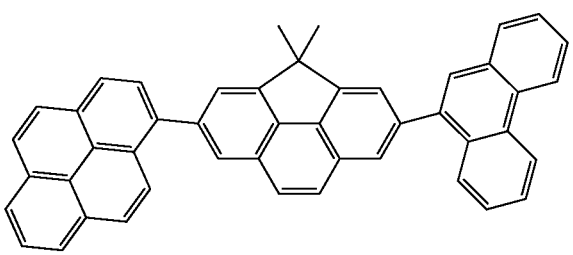
Chemical Formula 57

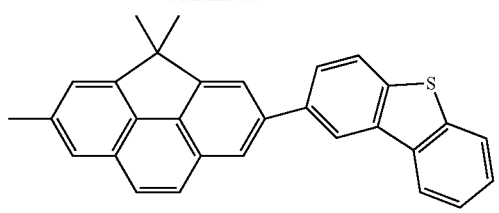
Chemical Formula 58
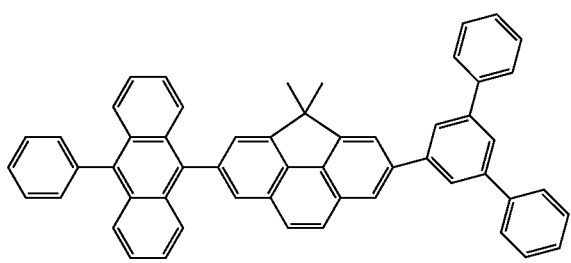
Chemical Formula 59
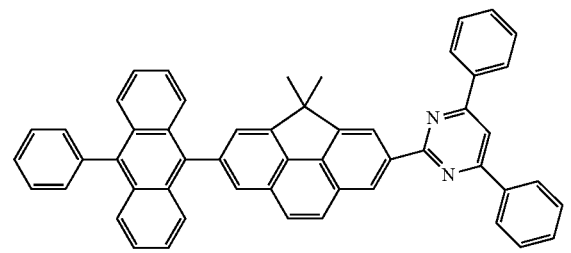
Chemical Formula 60
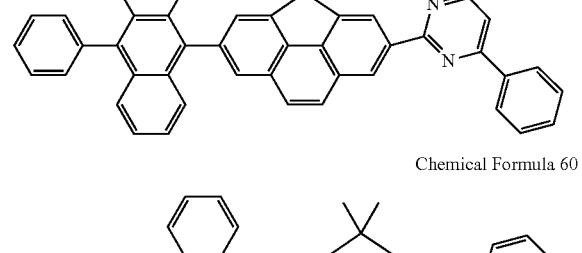
Chemical Formula 61
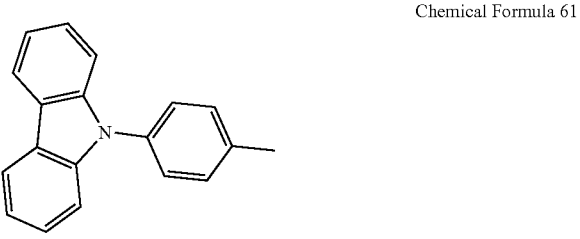
Chemical Formula 62
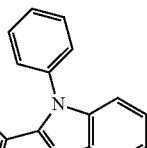
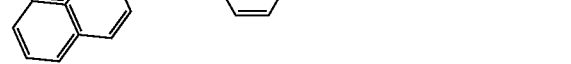
Chemical Formula 63
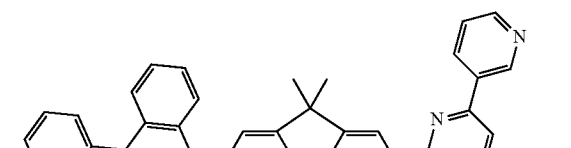
Chemical Formula 64
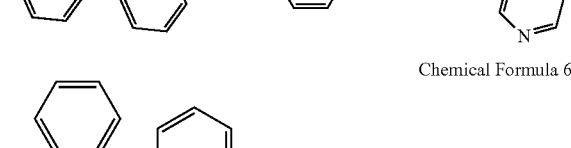
Chemical Formula 65
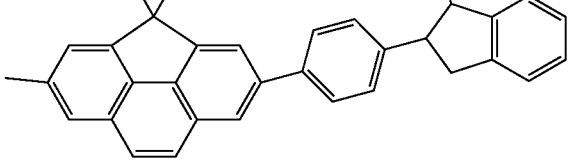
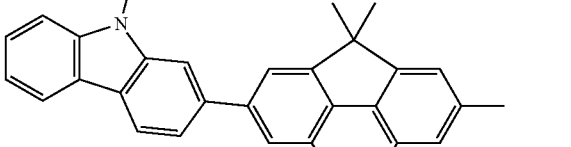
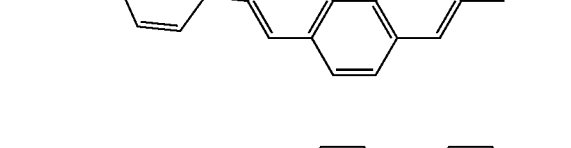
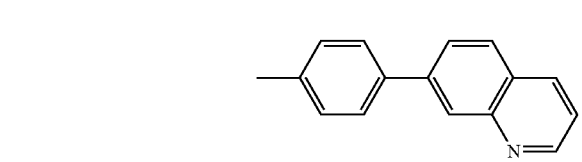

Chemical Formula 66
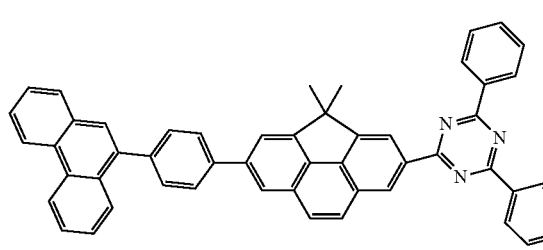
Chemical Formula 67
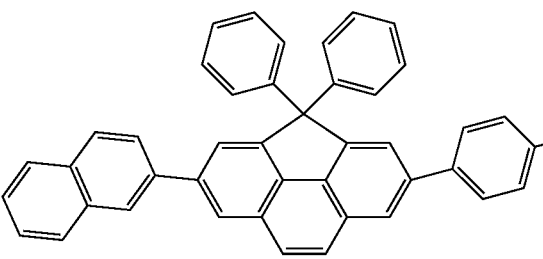
Chemical Formula 68
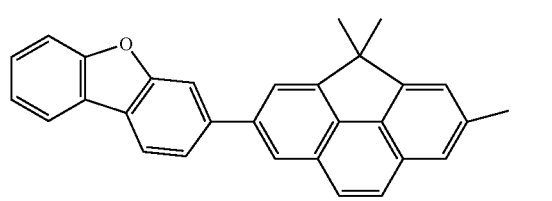
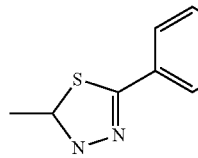
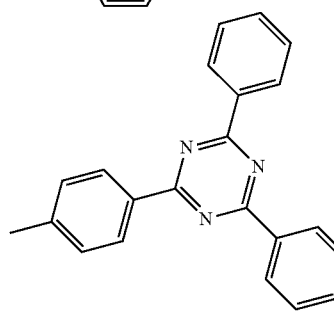
Chemical Formula 69
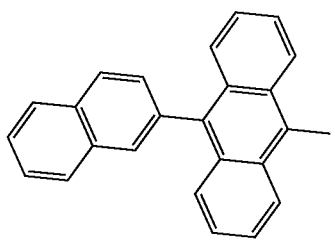
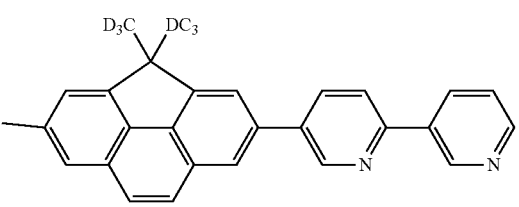
Chemical Formula 70
2. The organic compound of claim 1, wherein the compound is an organic compound including at least one selected from the following:
Chemical Formula 5
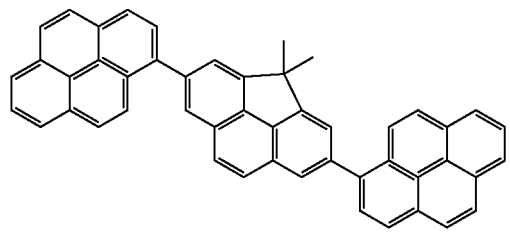
Chemical Formula 13
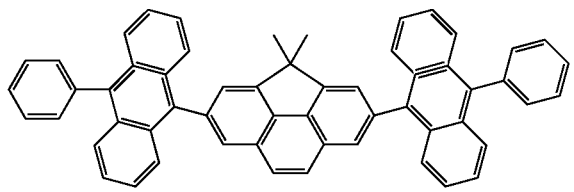

Chemical Formula 30
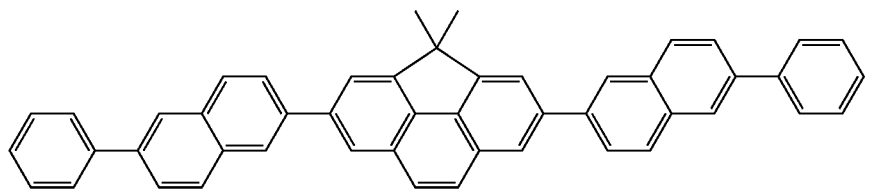
Chemical Formula 35
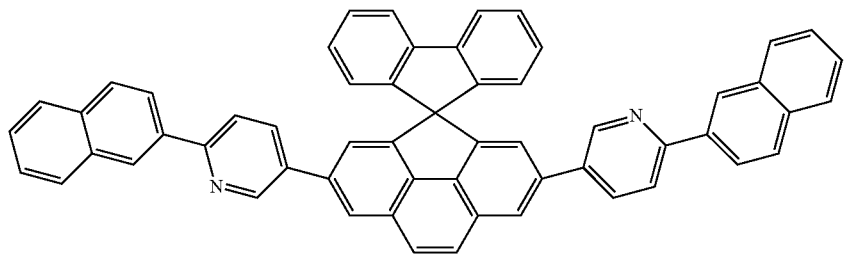
Chemical Formula 40
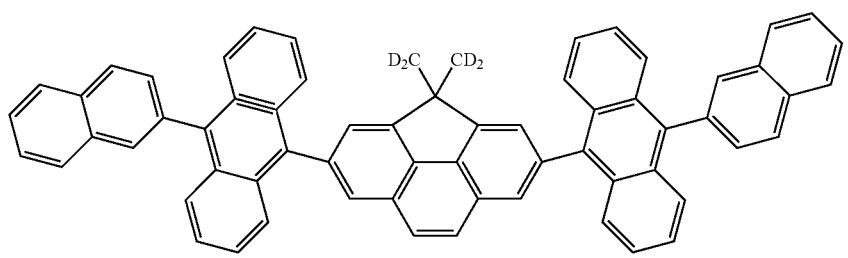
Chemical Formula 46
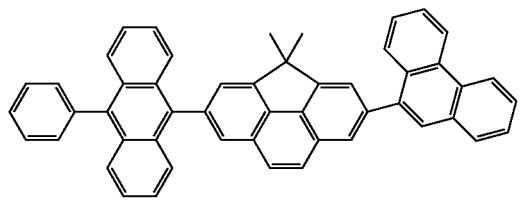
Chemical Formula 58
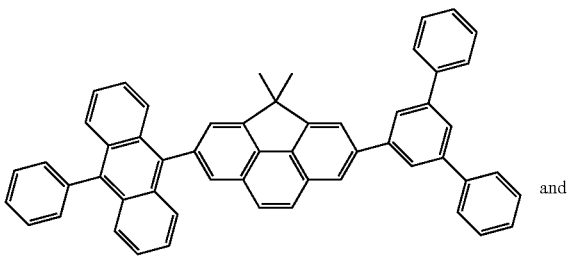
and
Chemical Formula 66
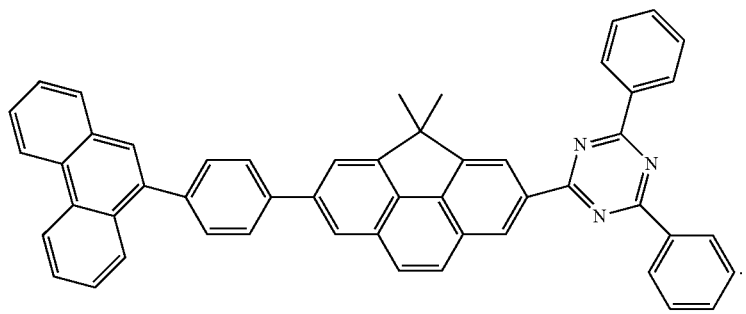

3. An organic light emitting diode device, comprising,
an anode,
a cathode, and
an organic layer interposed between the anode and cathode
wherein the organic layer comprises at least one organic compound selected from the compounds listed in the following Group 1

[Group 1]

Chemical Formula 2

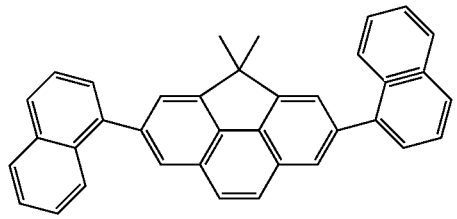

Chemical Formula 3

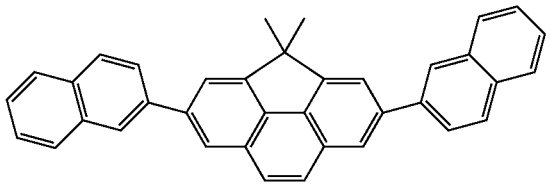

Chemical Formula 4

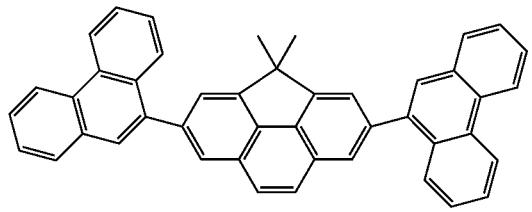

Chemical Formula 5

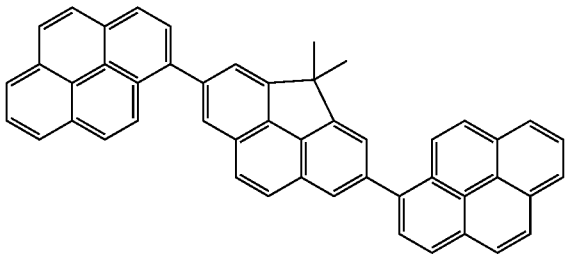

Chemical Formula 6

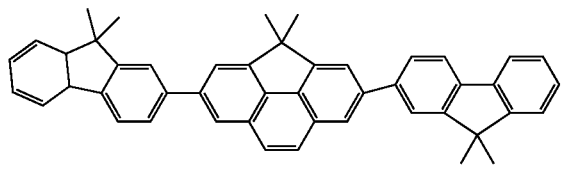

Chemical Formula 7

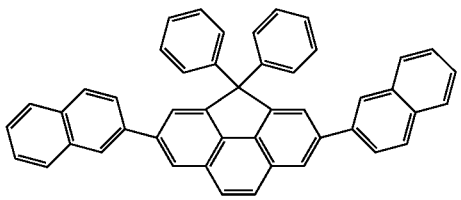

Chemical Formula 8

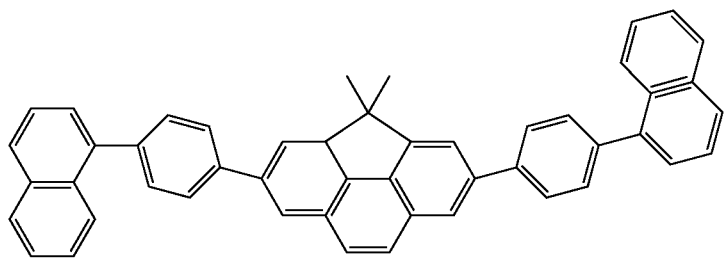

Chemical Formula 9

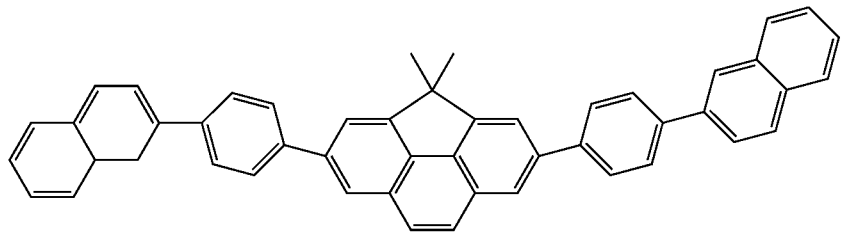

-continued
Chemical Formula 10
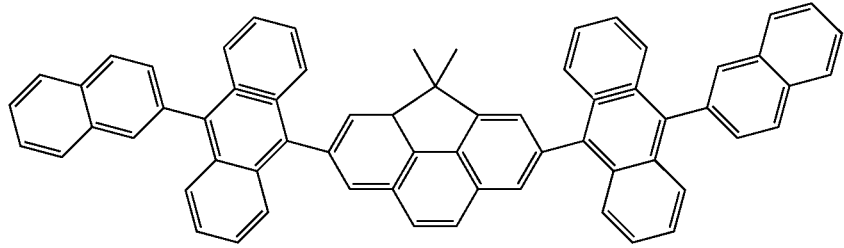
Chemical Formula 11
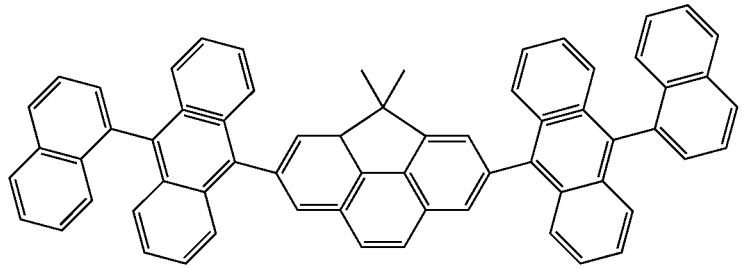
Chemical Formula 12
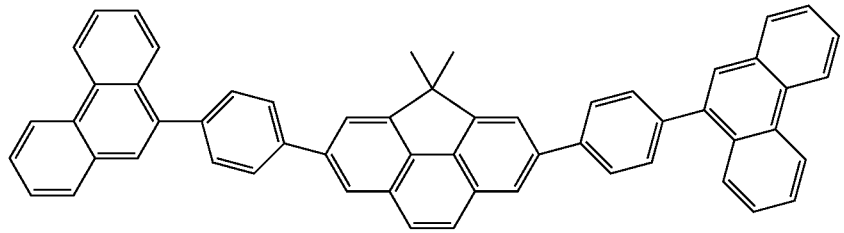
Chemical Formula 13
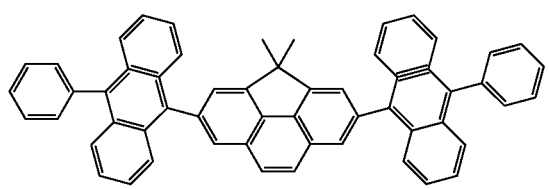
Chemical Formula 14
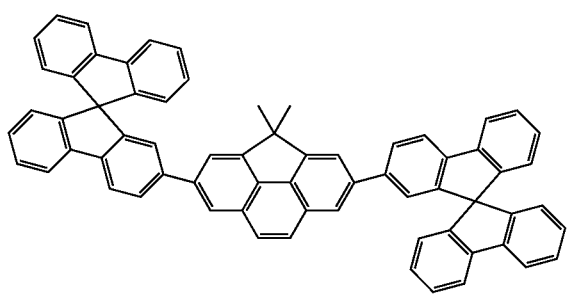
Chemical Formula 15
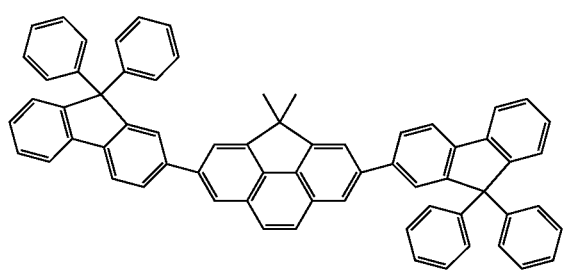
Chemical Formula 16
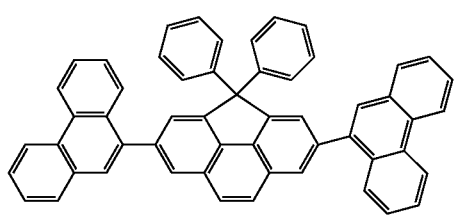
Chemical Formula 17
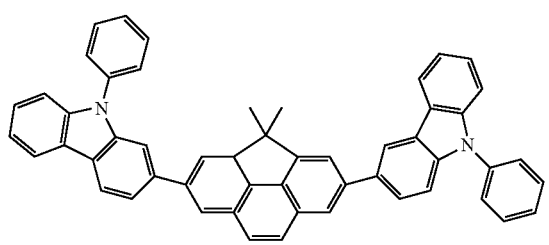
Chemical Formula 18
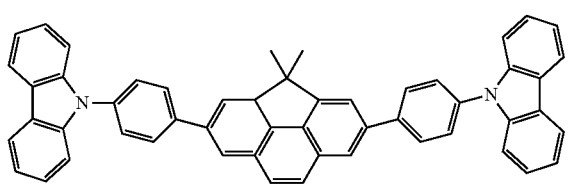

-continued
Chemical Formula 19
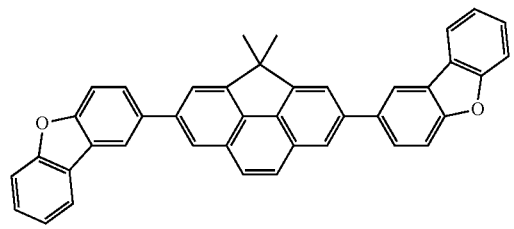
Chemical Formula 20
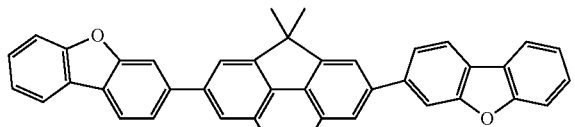
Chemical Formula 21
Chemical Formula 22
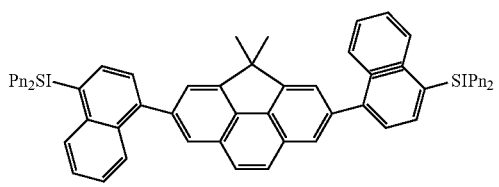
Chemical Formula 23
Chemical Formula 24
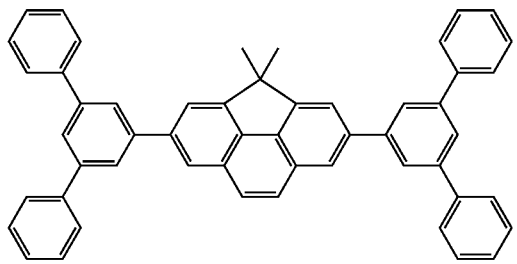
Chemical Formula 25
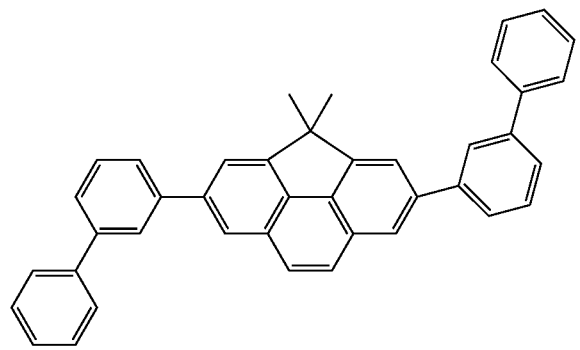
Chemical Formula 26
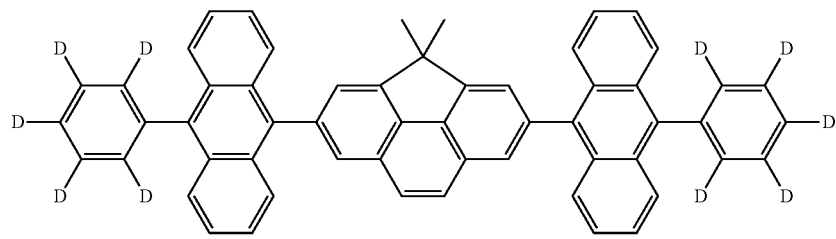
Chemical Formula 27
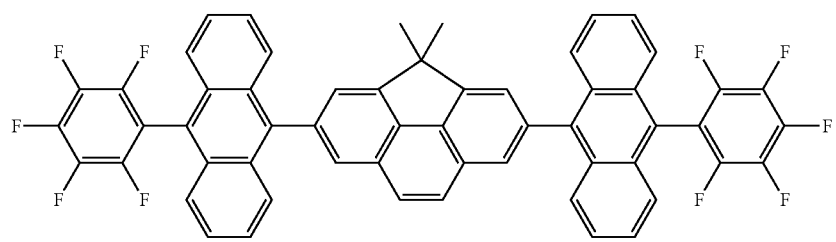

-continued
Chemical Formula 28
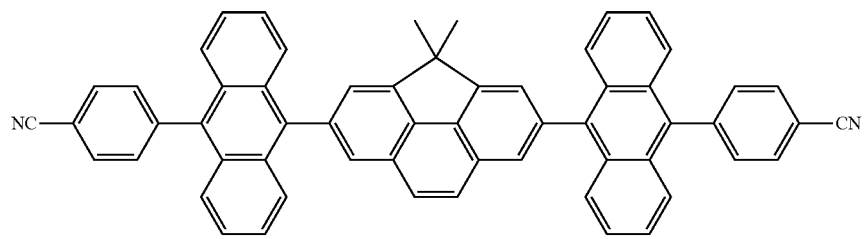
Chemical Formula 29
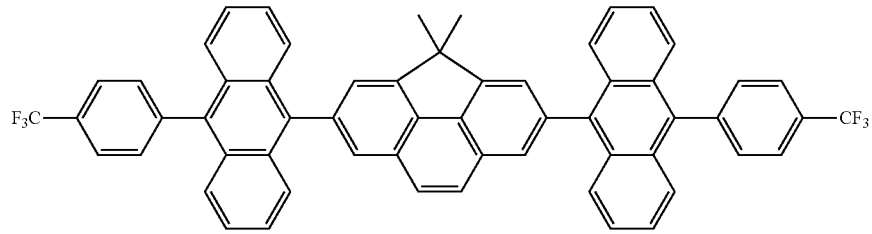
Chemical Formula 30
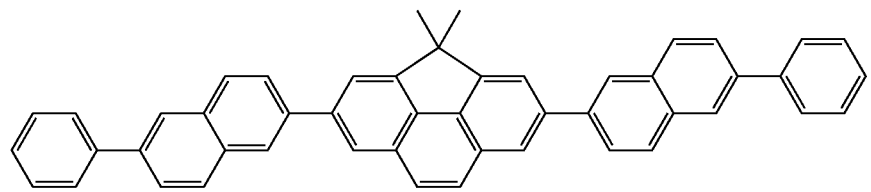
Chemical Formula 31
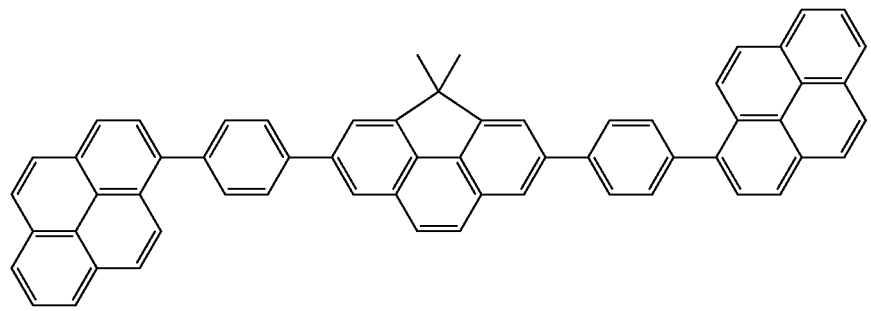
Chemical Formula 32
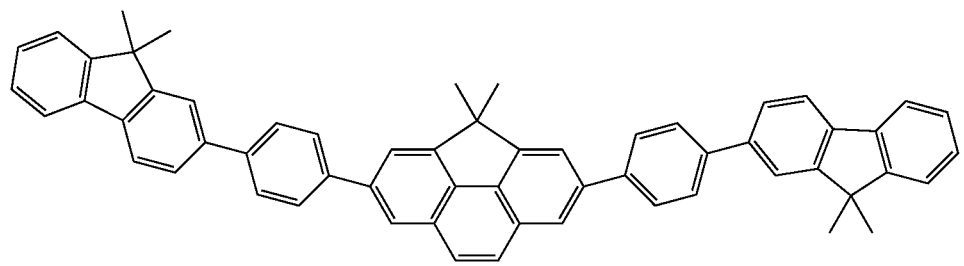
Chemical Formula 33
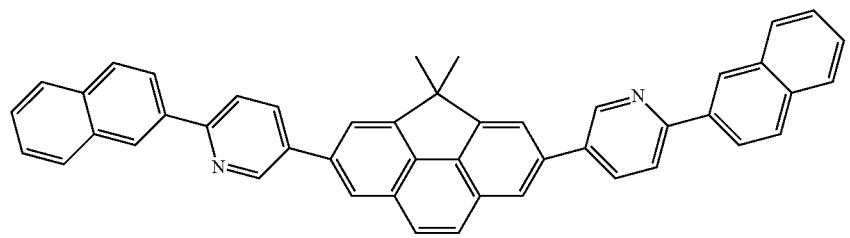

-continued
Chemical Formula 34
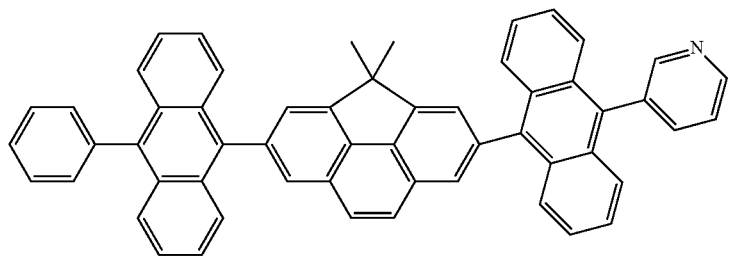
Chemical Formula 35
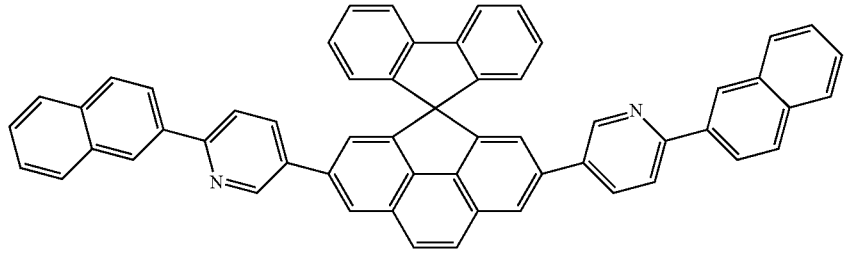
Chemical Formula 36
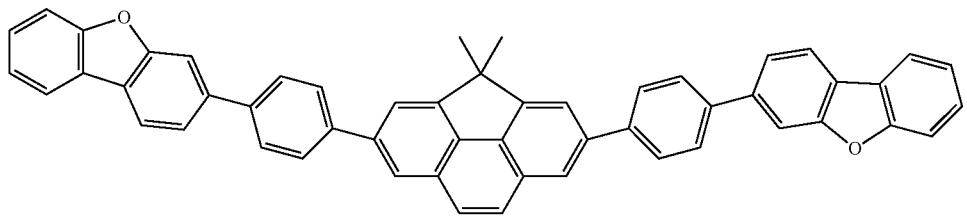
Chemical Formula 37
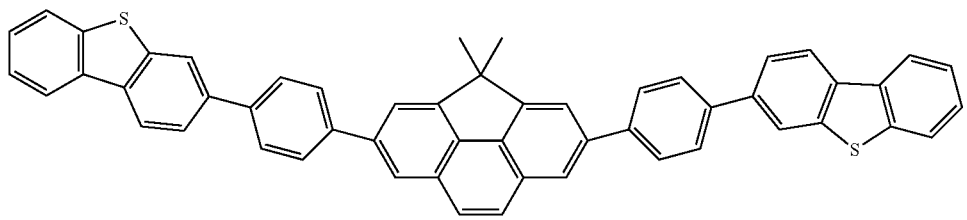
Chemical Formula 38
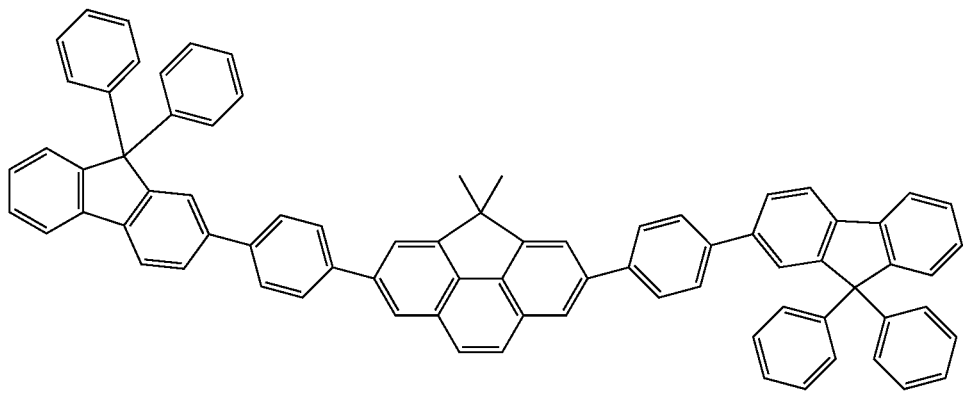

Chemical Formula 39
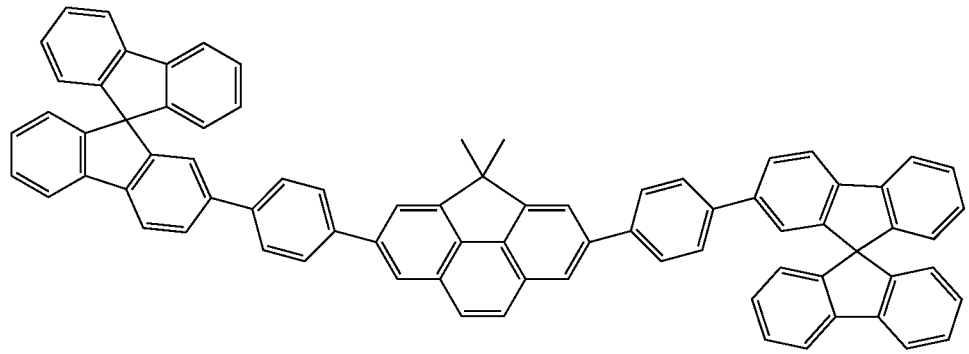
Chemical Formula 40
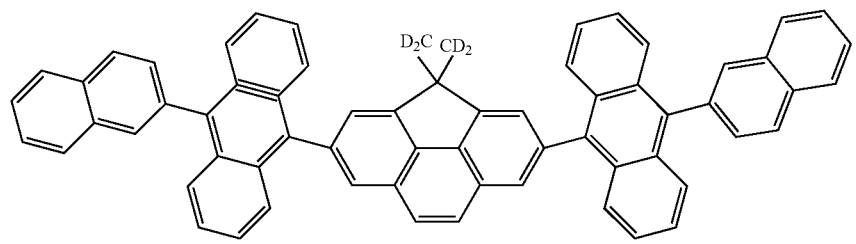
Chemical Formula 41
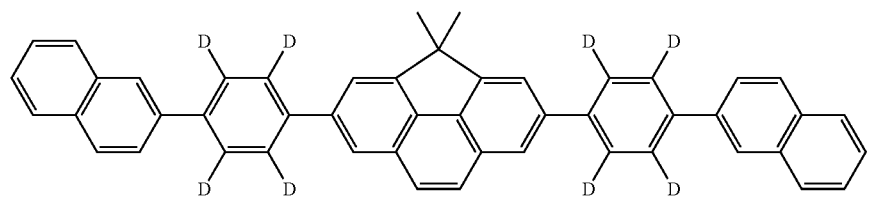
Chemical Formula 42
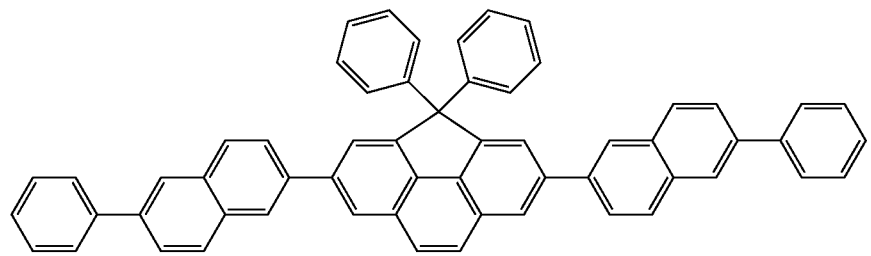
Chemical Formula 43
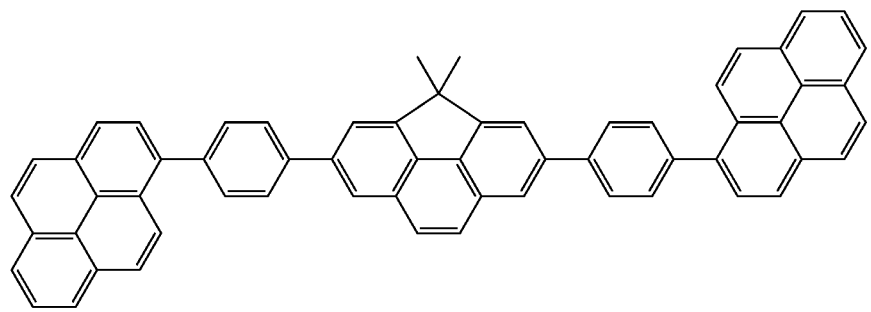

Chemical Formula 44
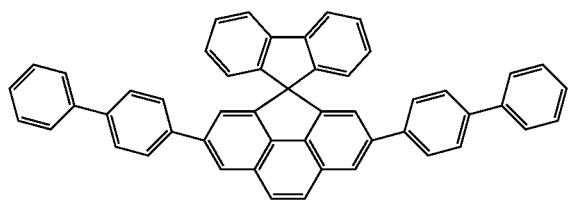
Chemical Formula 45
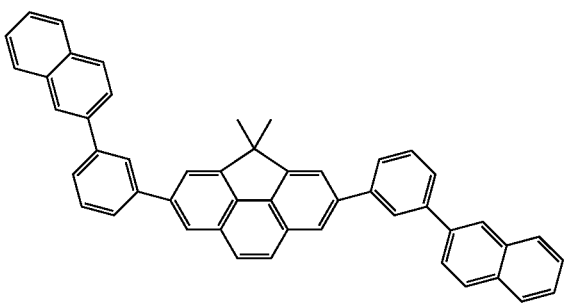
Chemical Formula 46
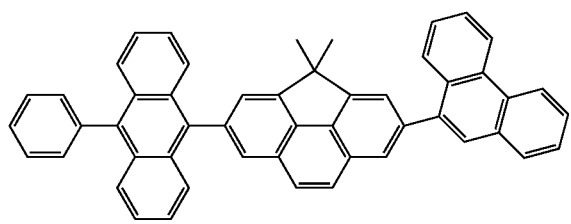
Chemical Formula 47
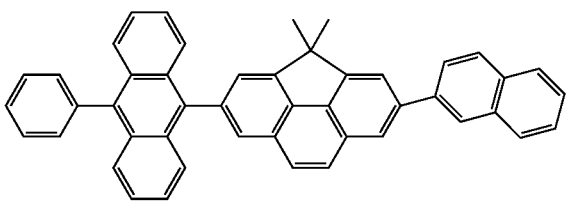
Chemical Formula 48
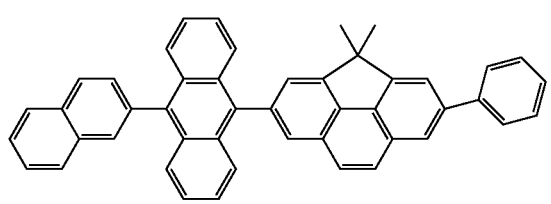
Chemical Formula 49
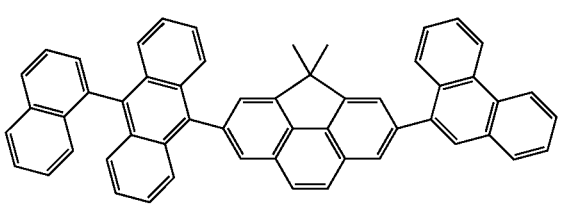
Chemical Formula 50
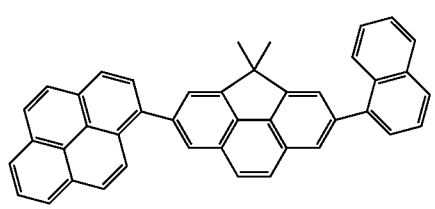
Chemical Formula 51
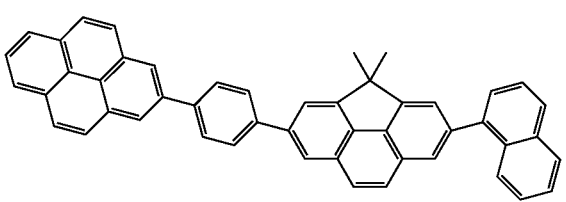
Chemical Formula 52
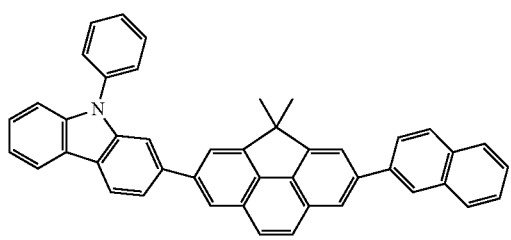
Chemical Formula 53
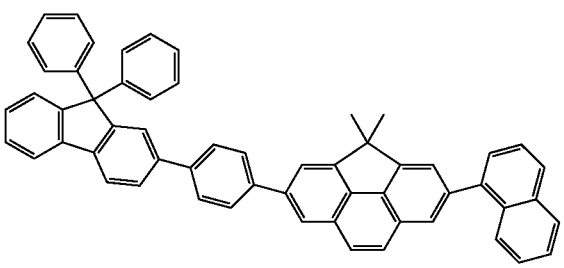
Chemical Formula 54
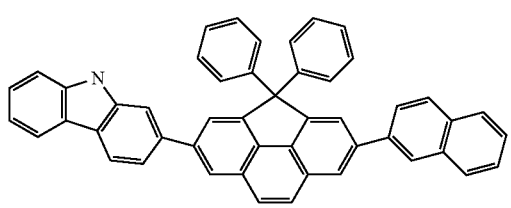
Chemical Formula 55
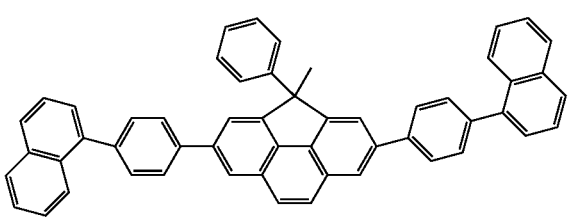

-continued
Chemical Formula 56
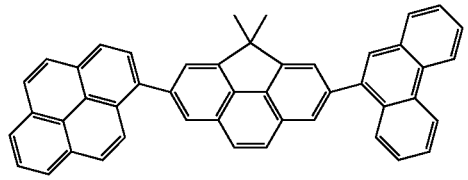
Chemical Formula 57
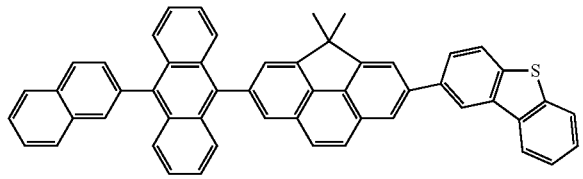
Chemical Formula 58
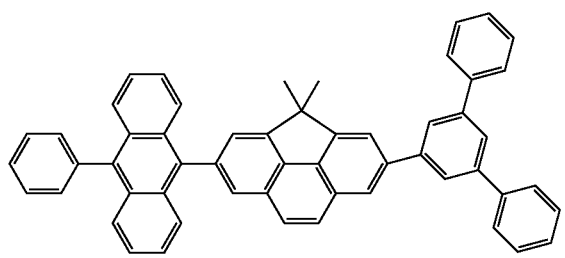
Chemical Formula 59
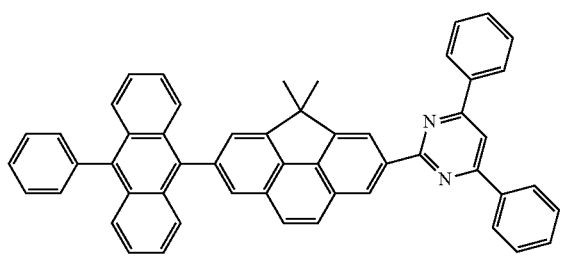
Chemical Formula 60
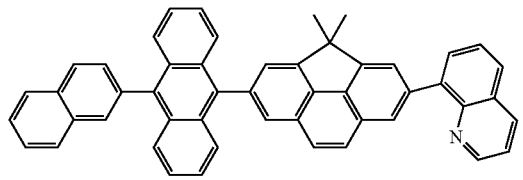
Chemical Formula 61
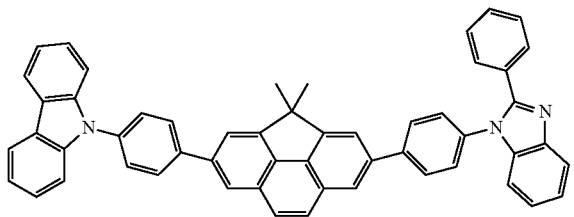
Chemical Formula 62
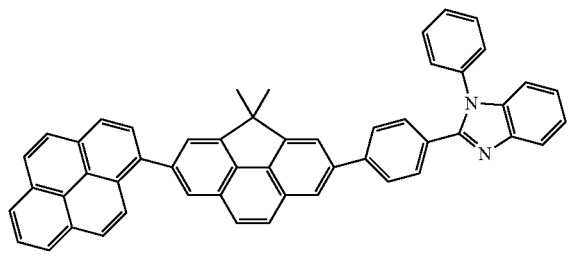
Chemical Formula 63
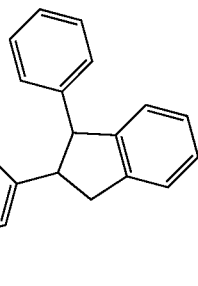
Chemical Formula 64
Chemical Formula 65
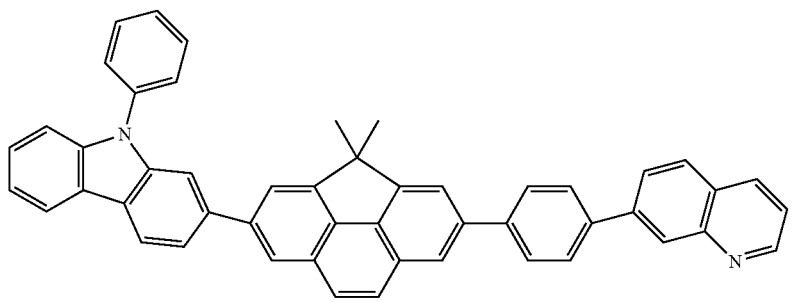

-continued
Chemical Formula 66
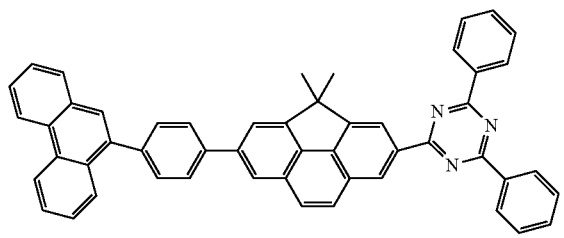
Chemical Formula 67
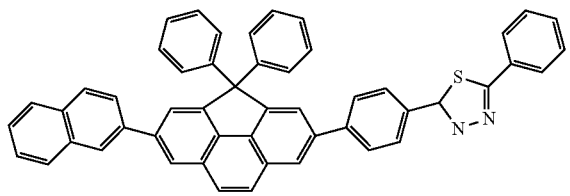
Chemical Formula 68
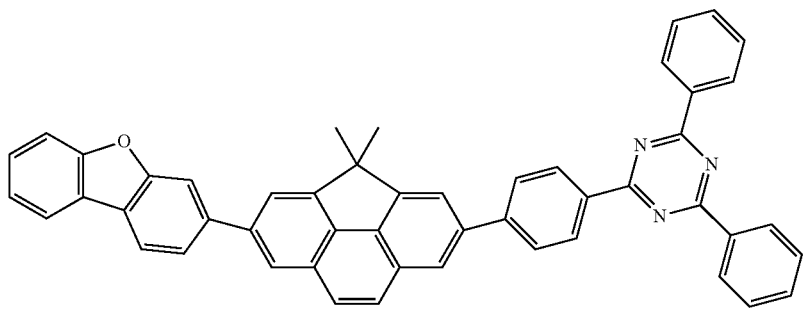
Chemical Formula 69
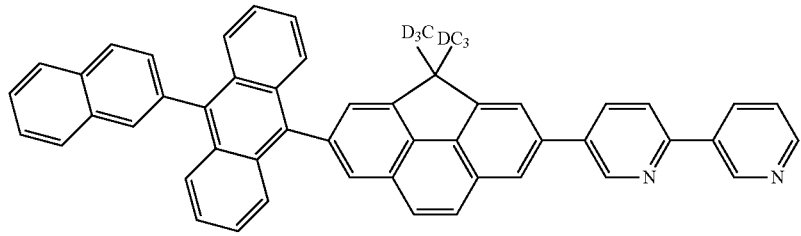
Chemical Formula 70
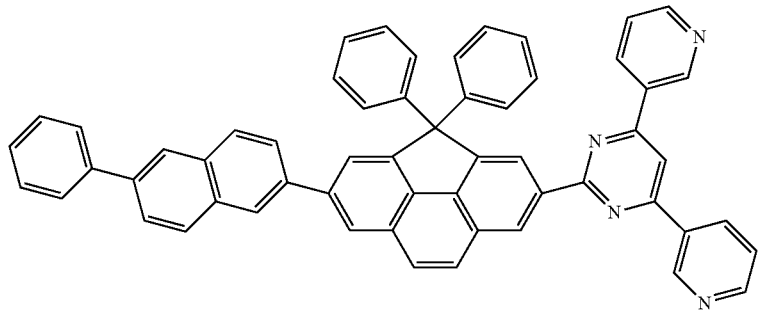
4. The organic light emitting diode device of claim 3, wherein the compound is an organic compound including at least one selected from the following:
Chemical Formula 5
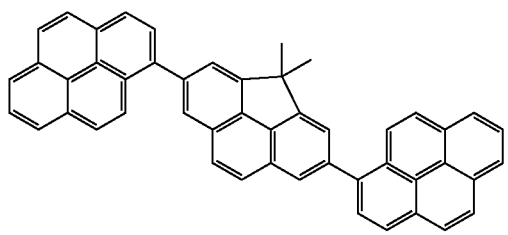
Chemical Formula 13
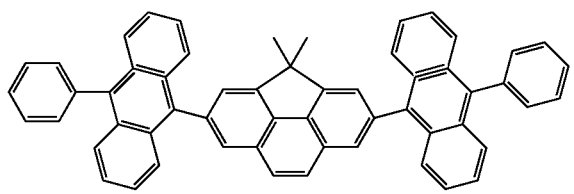

-continued

Chemical Formula 30
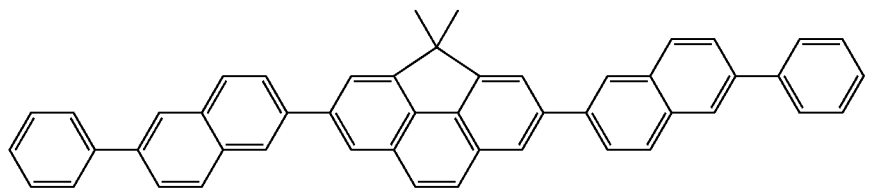

Chemical Formula 35
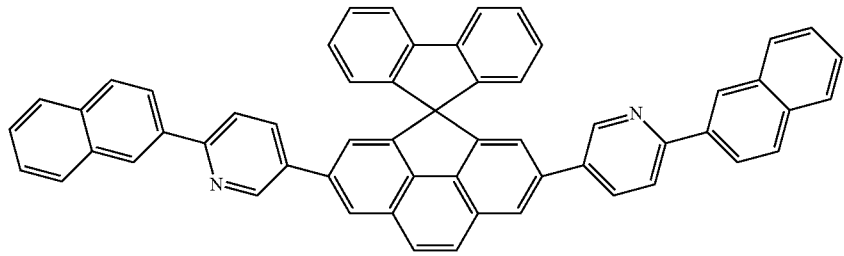

Chemical Formula 40
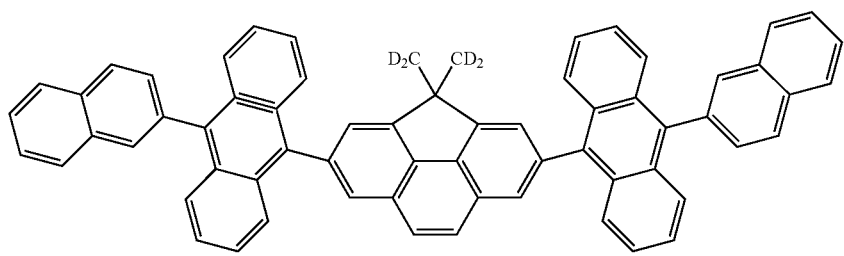

Chemical Formula 46
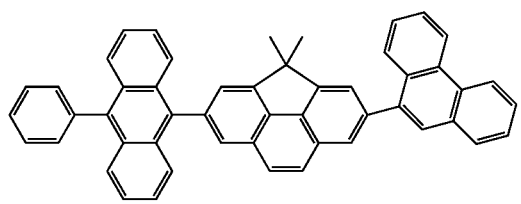

Chemical Formula 58
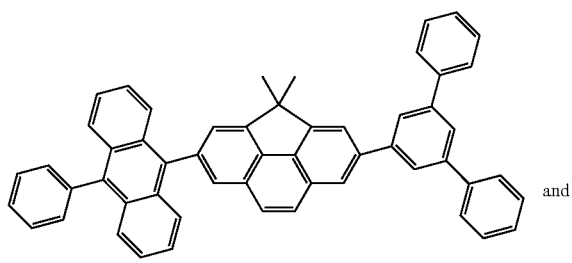

and

Chemical Formula 66
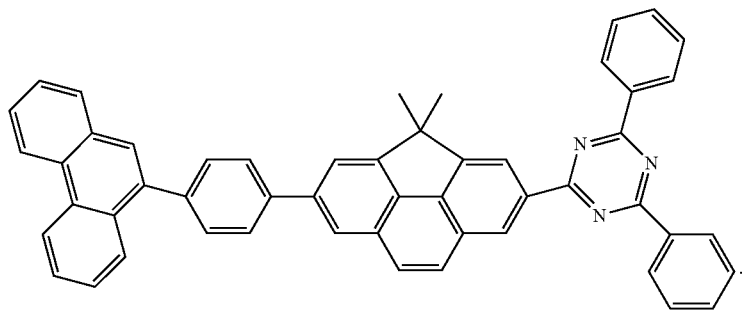

5. The organic light emitting diode device of claim 3, wherein the organic layer comprises an emission layer, and the organic compound is included in the emission layer.

6. The organic light emitting diode device of claim 5, wherein the emission layer further comprises anthracene, arylamine, styrene, a derivative thereof, or a combination thereof.

7. The organic light emitting diode device of claim 5, wherein the emission layer comprises the organic compound as a fluorescent or phosphorescent host.

8. The organic light emitting diode device of claim 3, wherein the organic layer comprises an emission layer, and an auxiliary layer interposed between the emission layer and the cathode, and the organic compound is included in the auxiliary layer.

9. The organic light emitting diode device of claim 8, wherein the emission layer comprises anthracene, arylamine, styrene, a derivative thereof, or a combination thereof.

* * * * *